(12) United States Patent
Charles et al.

(10) Patent No.: US 10,634,549 B2
(45) Date of Patent: Apr. 28, 2020

(54) HOSPITAL BED SCALE CALIBRATION METHODS AND PATIENT POSITION MONITORING METHODS

(71) Applicant: Hill-Rom Services, Inc., Batesville, IN (US)

(72) Inventors: Isaac J. Charles, Fuquay-Varina, NC (US); Unnati Ojha, Cary, NC (US); Michael Provinzano, Billerica, MA (US)

(73) Assignee: Hill-Rom Services, Inc., Batesville, IN (US)

( * ) Notice: Subject to any disclaimer, the term of this patent is extended or adjusted under 35 U.S.C. 154(b) by 392 days.

(21) Appl. No.: 15/428,457

(22) Filed: Feb. 9, 2017

(65) Prior Publication Data

US 2017/0234723 A1 Aug. 17, 2017

Related U.S. Application Data

(60) Provisional application No. 62/294,017, filed on Feb. 11, 2016.

(51) Int. Cl.
*G01G 23/01* (2006.01)
*A61B 5/11* (2006.01)
(Continued)

(52) U.S. Cl.
CPC ......... *G01G 23/012* (2013.01); *A61B 5/1036* (2013.01); *A61B 5/1115* (2013.01); *A61B 5/1118* (2013.01); *A61G 7/015* (2013.01); *A61G 7/0506* (2013.01); *A61G 7/0507* (2013.01); *A61G 7/0527* (2016.11); *G01G 19/445* (2013.01); *G01G 19/52* (2013.01); *G01G 23/01* (2013.01); *G08B 21/0461* (2013.01);
(Continued)

(58) Field of Classification Search
CPC .... G01G 23/012; G01G 19/52; G01G 19/445; G01G 23/01; A61G 7/015; A61G 7/0506; A61G 7/0507; A61G 7/0527; A61G 7/018; G08B 21/0461; A61B 5/1115; A61B 5/1118; A61B 5/1036; A61B 5/6892; A61B 2562/046; A61B 2560/0238; A61B 2562/0252
USPC .......................................................... 5/600
See application file for complete search history.

(56) References Cited

U.S. PATENT DOCUMENTS 4,015,677 A 4/1977 Silva et al.
4,023,633 A 5/1977 Swersey et al.
(Continued)

FOREIGN PATENT DOCUMENTS

EP 1974708 A4 6/2011
WO 2008040262 A1 4/2008

OTHER PUBLICATIONS

Extended European Search Report for EP Application EP3205268A1, dated Jul. 4, 2017, 9 pages.

*Primary Examiner* — Peter M. Cuomo
*Assistant Examiner* — Myles A Throop
(74) *Attorney, Agent, or Firm* — Barnes & Thornburg LLP

(57) ABSTRACT

A patient support apparatus includes a load frame, a support frame, and a plurality of load cells supporting the load frame on the support frame such that a load supported by the load frame is supported by the load cells, each load cell configured to produce a signal indicative of a load weight bearing upon that load cell. The load cells are calibrated after installation.

14 Claims, 16 Drawing Sheets

(51) Int. Cl.

| | | |
|---|---|---|
| *G01G 19/44* | (2006.01) | |
| *A61G 7/05* | (2006.01) | |
| *A61B 5/103* | (2006.01) | |
| *A61G 7/015* | (2006.01) | |
| *G01G 19/52* | (2006.01) | |
| *G08B 21/04* | (2006.01) | |
| *A61B 5/00* | (2006.01) | |
| *A61G 7/018* | (2006.01) | |

(52) U.S. Cl.
  CPC ..... *A61B 5/6892* (2013.01); *A61B 2560/0238* (2013.01); *A61B 2562/0252* (2013.01); *A61B 2562/046* (2013.01); *A61G 7/018* (2013.01)

(56) References Cited

U.S. PATENT DOCUMENTS

| | | | |
|---|---|---|---|
| 4,195,287 A | | 3/1980 | Mathis et al. |
| 4,228,426 A | | 10/1980 | Roberts |
| 4,242,672 A | | 12/1980 | Gault et al. |
| 4,295,133 A | | 10/1981 | Vance et al. |
| 4,363,368 A | | 12/1982 | Paddon et al. |
| 4,539,560 A | | 9/1985 | Fleck et al. |
| 4,550,793 A | | 11/1985 | Giles |
| 4,574,899 A | * | 3/1986 | Griffin .................. G01G 3/142 177/1 |
| 4,633,237 A | | 12/1986 | Tucknott et al. |
| 4,804,052 A | * | 2/1989 | Griffen ................ G01G 19/021 177/25.14 |
| 4,934,468 A | | 6/1990 | Koerber, Sr. et al. |
| 4,953,244 A | | 9/1990 | Koerber et al. |
| 4,961,470 A | | 10/1990 | Koerber, Sr. et al. |
| 5,276,432 A | | 1/1994 | Travis et al. |
| 5,279,144 A | * | 1/1994 | Levkowitch .......... G01G 23/01 16/367 |
| 5,606,516 A | | 2/1997 | Douglas et al. |
| 5,644,492 A | * | 7/1997 | Reichmuth .............. G01G 7/02 177/25.12 |
| 5,677,498 A | * | 10/1997 | Oakes .................... G01G 19/12 177/136 |
| 5,808,552 A | | 9/1998 | Wiley et al. |
| 5,823,278 A | * | 10/1998 | Geringer ................ G01G 19/52 177/144 |
| 5,831,221 A | | 11/1998 | Geringer et al. |
| 5,844,488 A | | 12/1998 | Musick |
| 6,067,019 A | * | 5/2000 | Scott ........................ A61B 5/11 340/562 |
| 6,080,106 A | | 6/2000 | Lloyd et al. |
| 6,133,837 A | | 10/2000 | Riley et al. |
| 6,208,250 B1 | | 3/2001 | Dixon et al. |
| 6,239,706 B1 | | 5/2001 | Yoshiike et al. |
| 6,438,776 B2 | | 8/2002 | Ferrand et al. |
| 6,518,520 B2 | | 2/2003 | Jones et al. |
| 6,636,820 B2 | | 10/2003 | Livingston |
| 6,668,408 B2 | | 12/2003 | Ferand et al. |
| 6,791,460 B2 | | 9/2004 | Dixon et al. |
| 6,822,571 B2 | | 11/2004 | Conway |
| 6,924,441 B1 | | 8/2005 | Mobley et al. |
| 6,969,809 B2 | | 11/2005 | Rainey |
| 7,100,439 B2 | | 9/2006 | Carlucci |
| 7,176,391 B2 | | 2/2007 | Metz et al. |
| 7,202,424 B2 | | 4/2007 | Carlucci |
| 7,292,150 B2 | | 11/2007 | Shaw |
| 7,310,839 B2 | | 12/2007 | Salvatini et al. |
| 7,335,839 B2 | | 2/2008 | Metz et al. |
| 7,557,718 B2 | | 7/2009 | Petrosenko et al. |
| 7,568,246 B2 | | 8/2009 | Weismiller et al. |
| 7,656,299 B2 | | 2/2010 | Gentry et al. |
| 7,666,151 B2 | | 2/2010 | Sullivan et al. |
| 7,698,765 B2 | | 4/2010 | Bobey et al. |
| 7,699,784 B2 | | 4/2010 | Wan Fong et al. |
| 7,834,768 B2 | | 11/2010 | Dixon et al. |
| 7,897,884 B2 | | 3/2011 | Harish |
| 7,973,666 B2 | | 7/2011 | Petrosenko et al. |
| 7,978,084 B2 | | 7/2011 | Dixon et al. |
| 7,987,069 B2 | | 7/2011 | Rodgers et al. |
| 8,048,005 B2 | | 11/2011 | Dixon et al. |
| 8,258,963 B2 | | 9/2012 | Dixon et al. |
| 8,272,087 B2 | | 9/2012 | Westermann |
| 8,344,860 B2 | | 1/2013 | Collins, Jr. et al. |
| 8,376,954 B2 | | 2/2013 | Lange et al. |
| 8,376,964 B2 | | 2/2013 | Park et al. |
| 8,381,336 B2 | | 2/2013 | Kazuno et al. |
| 8,403,865 B2 | | 3/2013 | Halperin et al. |
| 8,419,660 B1 | | 4/2013 | Shaw |
| 8,491,492 B2 | | 7/2013 | Shinar et al. |
| 8,517,953 B2 | | 8/2013 | Lange et al. |
| 8,525,679 B2 | | 9/2013 | Riley et al. |
| 8,525,680 B2 | | 9/2013 | Riley et al. |
| 8,537,008 B2 | | 9/2013 | Tallent et al. |
| 8,585,607 B2 | | 11/2013 | Klap et al. |
| 8,593,284 B2 | | 11/2013 | Tallent et al. |
| 8,598,893 B2 | | 12/2013 | Camus |
| 8,603,010 B2 | | 12/2013 | Lange et al. |
| 8,679,030 B2 | | 3/2014 | Shinar et al. |
| 8,689,376 B2 | | 4/2014 | Becker et al. |
| 8,731,646 B2 | | 5/2014 | Halperin et al. |
| 8,734,360 B2 | | 5/2014 | Klap et al. |
| 8,783,114 B2 | | 7/2014 | Anderson et al. |
| 8,838,411 B2 | | 9/2014 | Kazuno et al. |
| 8,840,564 B2 | | 9/2014 | Pinhas et al. |
| 8,844,073 B2 | | 9/2014 | Riley et al. |
| 8,844,076 B2 | | 9/2014 | Becker et al. |
| 8,882,684 B2 | | 11/2014 | Halperin et al. |
| 8,907,287 B2 | | 12/2014 | Vanderpohl |
| 8,921,717 B2 | | 12/2014 | Siegel et al. |
| 8,942,779 B2 | | 1/2015 | Halperin et al. |
| 8,973,186 B2 | | 3/2015 | Bhai |
| 8,992,434 B2 | | 3/2015 | Halperin et al. |
| 8,997,588 B2 | | 4/2015 | Taylor |
| 8,998,830 B2 | | 4/2015 | Halperin et al. |
| 9,009,893 B2 | | 4/2015 | Kramer et al. |
| 9,013,313 B2 | | 4/2015 | Paine |
| 9,013,315 B2 | | 4/2015 | Riley et al. |
| 9,026,199 B2 | | 5/2015 | Halperin et al. |
| 9,044,204 B2 | | 6/2015 | Riley et al. |
| 9,107,511 B2 | | 8/2015 | Skinner et al. |
| 9,131,902 B2 | | 9/2015 | Halperin et al. |
| 9,165,449 B2 | | 10/2015 | Ribble et al. |
| 9,311,804 B2 | | 4/2016 | Ribble |
| 9,320,444 B2 | | 4/2016 | Hayes et al. |
| 9,358,168 B2 | | 6/2016 | Williamson et al. |
| 9,383,250 B2 | | 7/2016 | Receveur et al. |
| 9,383,251 B2 | | 7/2016 | Dixon et al. |
| 9,506,106 B2 | | 11/2016 | Gough et al. |
| 9,549,675 B2 | | 1/2017 | Riley et al. |
| 9,549,705 B2 | | 1/2017 | Riley et al. |
| 9,552,460 B2 | | 1/2017 | Riley et al. |
| 9,552,714 B2 | | 1/2017 | Ribble et al. |
| 9,707,141 B2 | | 7/2017 | Bobey et al. |
| 9,754,476 B2 | | 9/2017 | Lemire et al. |
| 9,761,109 B2 | | 9/2017 | Ribble et al. |
| 2003/0010345 A1 | | 1/2003 | Koblasz et al. |
| 2004/0111045 A1 | | 6/2004 | Sullivan et al. |
| 2004/0118617 A1 | | 6/2004 | Carlucci |
| 2004/0163855 A1 | | 8/2004 | Carlucci |
| 2004/0168507 A1 | | 9/2004 | Nakada et al. |
| 2005/0273940 A1 | | 12/2005 | Petrosenko et al. |
| 2006/0028350 A1 | * | 2/2006 | Bhai .................... A61B 5/1115 340/666 |
| 2007/0157385 A1 | * | 7/2007 | Lemire .................. A61G 7/005 5/600 |
| 2007/0268147 A1 | | 11/2007 | Bhai |
| 2010/0300768 A1 | * | 12/2010 | Reiter .................... G01G 5/006 177/45 |
| 2011/0083271 A1 | | 4/2011 | Bhai |
| 2011/0085423 A1 | | 4/2011 | Cottrell |
| 2011/0112442 A1 | | 5/2011 | Meger et al. |
| 2011/0144455 A1 | | 6/2011 | Young et al. |
| 2011/0192429 A1 | | 8/2011 | Underwood et al. |
| 2011/0234408 A1 | | 9/2011 | Dixon et al. |
| 2012/0011941 A1 | | 1/2012 | Anderson et al. |
| 2012/0182148 A1 | | 7/2012 | Paine |

(56) References Cited

U.S. PATENT DOCUMENTS

| | | |
|---|---|---|
| 2012/0259248 A1 | 10/2012 | Receveur |
| 2013/0146371 A1 | 6/2013 | Shih |
| 2013/0270014 A1 | 10/2013 | Hu et al. |
| 2014/0124272 A1 | 5/2014 | Siegel et al. |
| 2014/0266733 A1 | 9/2014 | Hayes et al. |
| 2015/0101870 A1 | 4/2015 | Gough et al. |
| 2017/0254694 A1* | 9/2017 | Toigo .................. G01G 23/01 |

* cited by examiner

HOSPITAL BED SCALE CALIBRATION METHODS AND PATIENT POSITION MONITORING METHODS

CROSS-REFERENCE TO RELATED APPLICATIONS

This application claims priority under 35 U.S.C. § 119(e) to U.S. Provisional Application Ser. No. 62/294,017, filed Feb. 11, 2016, which is expressly incorporated by reference herein.

BACKGROUND

This application claims priority under 35 U.S.C. § 119(e) to U.S. Provisional Application Ser. No. 62/294,017, filed Feb. 11, 2016, which is expressly incorporated by reference herein.

The present disclosure is related to a patient support apparatus that includes a calibration system for calibrating the patient support apparatus to allow determination of a total weight of a patient placed on the patient support apparatus.

In a care facility, such as a hospital or a nursing home, patients are often placed on patient support apparatuses for an extended period of time. Patients who are positioned on the patient support apparatus for extended periods have an increased risk of developing certain complications or injuries, such as certain skin condition that may increase the potential of nosocomial pressure ulcers occurring. In an effort to mitigate or prevent such complications or injuries, some patient support apparatuses use load information gathered from an integrated scale system to derive pressure set points for a dynamic support surface, which continually redistributes the pressure of the dynamic support surface against the patient's skin. However, the weight attributable to the added or removed removable components while the patient remains on a patient support apparatus often causes errors in calculating the total weight of the patient, which in turn can lead to non-optimal pressure set points being derived from dynamic support surfaces.

In addition, caregivers often monitor the weight of a patient who is in a care facility to diagnose and treat certain medical conditions. For example, some caregivers closely monitor a patient's weight loss or weight gain throughout a course of treatment to determine, for example, whether the patient is retaining water. To facilitate making those determinations, some caregivers use an amount of weight calculated by the patient support apparatus upon which the patient is being supported. The weight attributable to added or removed removable components while the patient remains on the patient support apparatus may cause incorrect weight readings and result in incorrect diagnosis or treatment to certain medical conditions.

One system for monitoring a patient movement on a hospital bed is disclosed by U.S. Pat. No. 7,437,787, issued Oct. 21, 2008, which is assigned to the assignee of the present invention, and the disclosure of which is incorporated herein by reference for the teaching of using load cell signals for determining patient position.

SUMMARY

The present application discloses one or more of the features recited in the appended claims and/or the following features which, alone or in any combination, may comprise patentable subject matter:

According to the present disclosure, a patient support apparatus comprises a load frame, a support frame, a plurality of load cells, and a controller. The load cells support the load frame on the support frame such that a load supported by the load frame is supported by the load cells. Each load cell configured to produce a signal indicative of a load weight bearing upon that load cell. The controller determines the total weight supported by the load cells. A calibration constant for each respective load cell is determined dynamically by varying the magnitude and/or position of one or more calibration weights.

According to a first aspect of the present disclosure, a patient support apparatus comprises a load frame, a support frame, a plurality of load cells supporting the load frame on the support frame such that a load supported by the load frame is supported by the load cells, and a controller. Each load cell is configured to produce a signal indicative of a load weight bearing upon that load cell. The controller is coupled to the load cells to determine a total weight supported by the load cells. A calibration constant for each respective load cell is determined dynamically by varying the magnitude and/or position of one or more calibration weights.

In some embodiments, the controller comprises a processor and a memory device coupled to the processor, the memory device including instruction that, when processed by the processor cause the processor to consider the signal from each load cell and dynamically determines the calibration constants for the respective load cells. The calibration constants are determined by defining a plurality of load zones on a patient support surface defined by a plurality of predetermined calibration positions, detecting an object having a predefined calibration weight on one of a plurality of predetermined calibration positions on a patient support surface, measuring a current weight distribution of the predefined calibration weight on each of the load cells, storing a set of load weights for respective load cells that corresponds to the current distribution of the predefined calibration weight for each of the load cells at the predetermined calibration position and detecting the predefined calibration weight has been placed at a subsequent predetermined calibration positions. The measuring and storing steps are repeated for each subsequent calibration position. The controller then selects, subsequent to measuring and storing the load weights for the respective load cells at each predetermined calibration position, the predetermined calibration positions that define a first load zone. The controller then determines a set of calibration constants for respective load cells for first load zone using the selected load weights that correspond to each of the predetermined calibration positions that defines the first load zone. The steps of determining a set of calibration constants is repeated for each of a plurality of load zones to establish a plurality of sets of calibration constants for respective load cells that corresponds to each load zone such that each of the plurality of sets of calibration constants corresponds to a respective one of the plurality of load zones.

In some embodiments, the controller is further configured to determine a current position of the patient by determining a current weight distribution of patient weight, determine a load zone that corresponds to the current position of the patient, select the set of calibration constants that corresponds to the load zone, and determine, using the selected set of calibration constants, the actual weight of the patient supported on the patient support apparatus.

In some embodiments, the plurality of predetermined calibration positions includes at least five predetermined calibration positions including a center of the patient support surface, the plurality of predetermined calibration positions further defines a plurality of load zones by connecting the predetermined calibration position at the center of the patient support surface with at least three other predetermined calibration positions, such that the total number of predetermined calibration positions for a load zone equal to the number of load cells.

In some embodiments, the controller comprises a processor and a memory device coupled to the processor, the memory device including instructions that, when processed by the processor, cause the processor to consider the signal from each load cell and dynamically determine the calibration constants for the respective load cells by defining a plurality of weight ranges, detecting a first object having a first representative calibration weight that falls within one of the plurality of weight ranges on one of a plurality of predetermined calibration positions of the patient support surface, measuring a current weight distribution of the first representative calibration weight on each of the load cells, storing a set of load weights for respective load cells that corresponds to the current distribution of the first representative calibration weight for each of the load cells at the predetermined calibration position, detecting the first representative calibration weight has been placed at a subsequent calibration positions and executing the detecting of the object and measuring weight distribution steps at each subsequent calibration position. The controller may further detect the first object having the first representative calibration weight has been removed, and establish a plurality sets of load weights for respective load cells that corresponds to each of the representative calibration weight by for each of the plurality of representative calibration weights, and determining, using the plurality of sets of load weights that corresponds to respective representative calibration weights, a plurality of sets of calibration constants that corresponds to each of the weight ranges.

In some embodiments, the controller is configured to determine an estimated weight of patient supported on a patient support surface using a set of initial calibration constants, select a set of calibration constants that corresponds to the estimated weight of the patient, and determine, using the selected set of calibration constants, the actual weight of the patient supported on the patient support apparatus.

In some embodiments, the controller comprises a processor and a memory device coupled to the processor, the memory device including instructions that, when processed by the processor, cause the processor to consider the signal from each load cell and dynamically determines the calibration constants for the respective load cells by detecting a predefined calibration weight on a patient support surface at one of "n" calibration positions, wherein n is a numerical number greater than four, measuring a current weight distribution of the predefined calibration weight on each of the load cells, storing a set of load weights for respective load cells that corresponds to the current distribution of the predefined calibration weight for each of the load cells, detecting the predefined calibration weight has been placed at a subsequent predetermined calibration positions and repeating at each subsequent calibration position. The controller may also select, subsequent to establishing "n" sets of calibration constants for each of the load cells, four sets of calibration constants randomly from the "n" sets of calibration constants, and determine a set of calibration constants for respective load cells by averaging the selected calibration constants.

In some embodiments, the controller is configured to determine an actual weight of the patient supported on the patient support apparatus by using the determined set of calibration constants for respective load cells.

In some embodiments, the controller is configured to trigger an alarm when a rate of change in patient position exceeds an alarm threshold.

In some embodiments, the alarm threshold depends on a patient activity level.

In some embodiments, the controller further comprises a memory configured to store a plurality of alarm thresholds that corresponds to each patient activity level.

In some embodiments, the patient activity level is predefined by a user.

In some embodiments, the controller is configured to determine the patient activity level by determining a rate of changes in the weight distribution on each of the plurality of load cells for a predetermined time period.

According to a second aspect of the present disclosure, a patient support apparatus comprises a load frame, a support frame, a plurality of load cells supporting the load frame on the support frame such that a load supported by the load frame is supported by the load cells, and a controller. Each load cell is configured to produce a signal indicative of a load weight bearing upon that load cell. The controller is coupled to the load cells to determine a total weight supported by the load cells. A plurality of calibration constants are determined for each respective load cell, and a calibration constant to be applied to each load cell signal being determined based on the location of the load weight on the load frame.

In some embodiments, the controller comprises a processor and a memory device coupled to the processor, the memory device including instruction that, when processed by the processor cause the processor to consider the signal from each load cell and dynamically determines the calibration constants for the respective load cells. The calibration constants are determined by defining a plurality of load zones on a patient support surface defined by a plurality of predetermined calibration positions, detecting an object having a predefined calibration weight on one of a plurality of predetermined calibration positions on a patient support surface, measuring a current weight distribution of the predefined calibration weight on each of the load cells, storing a set of load weights for respective load cells that corresponds to the current distribution of the predefined calibration weight for each of the load cells at the predetermined calibration position and detecting the predefined calibration weight has been placed at a subsequent predetermined calibration positions. The measuring and storing steps are repeated for each subsequent calibration position. The controller then selects, subsequent to measuring and storing the load weights for the respective load cells at each predetermined calibration position, the predetermined calibration positions that define a first load zone. The controller then determines a set of calibration constants for respective load cells for first load zone using the selected load weights that correspond to each of the predetermined calibration positions that defines the first load zone. The steps of determining a set of calibration constants is repeated for each of a plurality of load zones to establish a plurality of sets of calibration constants for respective load cells that corresponds to each load zone such that each of the plurality of sets of calibration constants corresponds to a respective one of the plurality of load zones.

In some embodiments, the controller is further configured to determine a current position of the patient by determining a current weight distribution of patient weight, determine a load zone that corresponds to the current position of the patient, select the set of calibration constants that corresponds to the load zone, and determine, using the selected set of calibration constants, the actual weight of the patient supported on the patient support apparatus.

In some embodiments, the plurality of predetermined calibration positions includes at least five predetermined calibration positions including a center of the patient support surface, the plurality of predetermined calibration positions further defines a plurality of load zones by connecting the predetermined calibration position at the center of the patient support surface with at least three other predetermined calibration positions, such that the total number of predetermined calibration positions for a load zone equal to the number of load cells.

In some embodiments, the controller is configured to trigger an alarm when a rate of change in patient position exceeds an alarm threshold.

In some embodiments, the alarm threshold depends on a patient activity level.

In some embodiments, the controller further comprises a memory configured to store a plurality of alarm thresholds that corresponds to each patient activity level.

According to a third aspect of the present disclosure, a system for monitoring a patient comprises a patient support surface configured to support the patient, a plurality of load cells each configured to produce a signal indicative of an amount of weight bearing upon that load cell, a controller responsive to the signals produced by the plurality of load cells to determine a current distribution of patient weight on each of the load cells, and a memory having stored the distribution of patient weight on each of the load cells for a predetermined time period. The controller is configured to determine patient position by determining the rate of changes in weight distribution compared to a patient activity level threshold.

In some embodiments, the memory further stores therein the plurality of sets of conditions defining threshold values for each of the load cells corresponding to each of the patient positions on the patient support surface.

According to a fourth aspect of the present disclosure, a method for determining weight of a patient supported on a patient support apparatus, comprising steps of establishing "n" load zones, wherein n is greater than one, determining a loci of a centroid of a patient load using first calibration constants, determining the load zone, applying second calibration constants corresponding to the load zone, and determining weight.

According to a fifth aspect of the present disclosure, a method for calibrating a patient support apparatus, comprises the steps of placing an object having a predefined calibration weight on one of a plurality of discrete predetermined positions on a patient support surface, wherein the plurality of discrete predetermined positions includes a center of the patient support surface, measuring a current weight distribution of the predefined calibration weight on each of the load cells, storing a set of load weights for each of the load cells that corresponds to the current distribution of the predefined calibration weight on each of the load cells at the discrete placement, defining as one of a plurality of sets of weight distribution a set of normalized threshold values corresponding to the placement of the predefined calibration weight on each of the load cells, moving the predefined calibration weight on a different load cell and executing the measuring, storing, and defining steps at each of the load cells, repeating the previous steps to establish a plurality of sets of calibration constants for each of the load cells, placing a patient on the patient support surface, determining a position of the patient by determining a weight distribution within any one or more of the number of different zones of the mattress, selecting the set of calibration constants corresponding to the weight distribution on the patient support surface, and using the selected set of calibration constants to determine the weight of the patient.

According to a sixth aspect of the present disclosure, a method for determining weight of a patient supported on a patient support apparatus comprises the steps of establishing a plurality of sets of calibration constants for each load cells, each of the plurality of sets of calibration constants corresponding to one of a plurality of predetermined calibration positions on a patient support surface, the plurality of predetermined calibration positions further defining a plurality of load zones of the patient support surface, determining a current distribution of patient weight within the plurality of the load zones, selecting the set of calibration constants that corresponds to the current distribution of the patient weight within the load zones, determining a position of the patient that corresponds to the set of calibration constants, and determining, using the selected set of calibration constants, the weight of the patient supported on the patient support apparatus.

In some embodiments, the plurality of predetermined calibration positions includes at least five predetermined calibration positions including a center of the patient support surface and on each of the load cells, the plurality of predetermined calibration positions further defining a plurality of load zones by connecting the predetermined calibration position at the center of the patient support surface and at least two other predetermined calibration positions.

In some embodiments, establishing a plurality of sets of calibration constants includes placing an object having a predefined calibration weight on one of a plurality of predetermined calibration positions on a patient support surface, measuring a current weight distribution of the predefined calibration weight on each of the load cells, storing a set of load weights of each of the load cells that corresponds to the current distribution of the predefined calibration weight on each of the load cells at the predetermined calibration position, moving the predefined calibration weight on a predetermined calibration position and executing the measuring and storing steps at each predetermined calibration position of the predefined calibration weight, establishing a plurality sets of load weights that corresponds to each of the predetermined calibration positions, determining, using the plurality sets of load weights, the plurality of sets of calibration constants that corresponds to each of the predetermined calibration positions, and establishing the plurality of sets of calibration constants.

In some embodiments, establishing a plurality of sets of calibration constants further includes forming a data table populated by the plurality of sets of calibration constants with each of the plurality of sets of calibration constants defined by a corresponding set of the load weights for each of the load cells and a corresponding set of the weight distribution within each of the load zones.

According to a seventh aspect of the present disclosure, a system for monitoring a patient comprises a patient support surface configured to support the patient, a plurality of load cells each configured to produce a signal indicative of an amount of weight bearing upon that load cell, at least five predetermined calibration positions, each of which sequentially receives a predefined calibration weight, a plurality of load zones defined by at least three of the predetermined calibration positions, a controller responsive to the signals produced by the plurality of load cells to determine calibration constants for each of the load cells, and a memory having stored the plurality of sets of calibration constants that corresponds to a different weight distribution on the patient support surface. The controller is configured to (i) determine a patient position by determining the current distribution of a patient weight within each of the plurality of load zones of the patient support surface, (ii) selects the set of calibration constants that corresponds to the patient position, and (iii) determine the weight of the patient using the selected calibration constants.

According to an eighth aspect of the present disclosure, a method for determining weight of a patient supported on a patient support apparatus comprises the steps of establishing a plurality of sets of calibration constants for each of the load cells, determining an estimated weight of patient supported on a patient support surface using default calibration constants, selecting the set of calibration constants that corresponds to the estimated weight of the patient, and determining, using the selected set of calibration constants, the weight of the patient supported on the patient support apparatus.

In some embodiments, the plurality of sets of calibration constants includes placing an object having a predefined calibration weight on one of a plurality of predetermined calibration positions of the patient support surface, each of the predetermined calibration positions corresponds to a position of the load cells, measuring a current weight distribution of the predefined calibration weight on each of the load cells, storing a set of load weights on each of the load cells that corresponds to the current distribution of the predefined calibration weight on each of the load cells, moving the predefined calibration weight on each of the predetermined calibration positions and executing the measuring and storing steps at each of the predetermined calibration positions of the predefined calibration weight, removing the object having the predefined calibration weight, repeating the previous steps with an object having a different predefined calibration weight, establishing a plurality sets of load weights on each of the load cells that corresponds to each of the predefined calibration weight, determining, using the plurality sets of load weights, the plurality of sets of calibration constants that corresponds to each of the predefined calibration weights, and establishing the plurality of sets of calibration constants.

In some embodiments, establishing a plurality of sets of calibration constants further includes forming a data table populated by the plurality of sets of calibration constants with each of the plurality of sets of calibration constants defined by a corresponding set of the load weights on each of the load cells for each of the predefined calibration weights, wherein each of the calibration constant corresponds to each of the predefined calibration weight which represents one of a plurality of ranges of possible patient weights.

In some embodiments, establishing a plurality of sets of calibration constants includes placing each of the predefined calibration weights on each of the predetermined calibration positions of the patient support surface, each of the predefined calibration weights being a same weight, measuring a current weight distribution of the predefined calibration weight on each of the load cells, storing a set of load weights on each of the load cells that corresponds to the current distribution of the predefined calibration weights on each of the load cells, removing the object having the predefined calibration weight, repeating the previous steps with different predefined calibration weights, each of the predefined calibration weights being a same weight, establishing a plurality sets of load weights on each of the load cells that corresponds to each of the predefined calibration weights, determining, using the plurality sets of load weights, the plurality of sets of calibration constants that corresponds to each of the predefined calibration weights, and establishing the plurality of sets of calibration constants.

According to a ninth aspect of the present disclosure, a method for calibrating a patient support apparatus comprises the steps of placing a predefined calibration weight on a patient support surface at one of "n" calibration positions, wherein n is a numerical number greater than four, measuring a current weight distribution of the predefined calibration weight on each of the load cells, storing a set of load weights on each of the load cells that corresponds to the current distribution of the predefined calibration weight on each of the load cells, moving the predefined calibration weight on each of the predetermined calibration positions and executing the measuring and storing steps at each of the predetermined calibration positions of the predefined calibration weight, selecting, subsequent to establishing "n" sets of calibration constants for each of the load cells, four sets of calibration constants randomly from the "n" sets of calibration constants, and determining a true calibration constant for each of the load cells by averaging the selected calibration constants.

According to a tenth aspect of the present disclosure, a method for calibrating a patient support apparatus comprises the steps of placing an object having a predefined calibration weight on one of a plurality of predetermined calibration positions on a patient support surface, measuring a current weight distribution of the predefined calibration weight on each of the load cells, storing a set of load weights of each of the load cells that corresponds to the current distribution of the predefined calibration weight on each of the load cells at the predetermined calibration position, moving the predefined calibration weight on a predetermined calibration position and executing the measuring and storing steps at each predetermined calibration position of the predefined calibration weight, establishing a plurality sets of load weights that corresponds to each of the predetermined calibration positions, determining, using the plurality sets of load weights, the plurality of sets of calibration constants that corresponds to each of the predetermined calibration positions, and establishing the plurality of sets of calibration constants.

In some embodiments, the predetermined calibration positions are different from positions of the plurality of load cells.

In some embodiments, the plurality of load cells is positioned near the four corners of the patient support apparatus.

In some embodiments, a first calibration position is between the first load cell and the second load cell.

In some embodiments, a second calibration position is between the second load cell and the third load cell.

In some embodiments, a third calibration position is between the third load cell and the fourth load cell.

In some embodiments, a fourth calibration position is between the fourth load cell and the first load cell.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
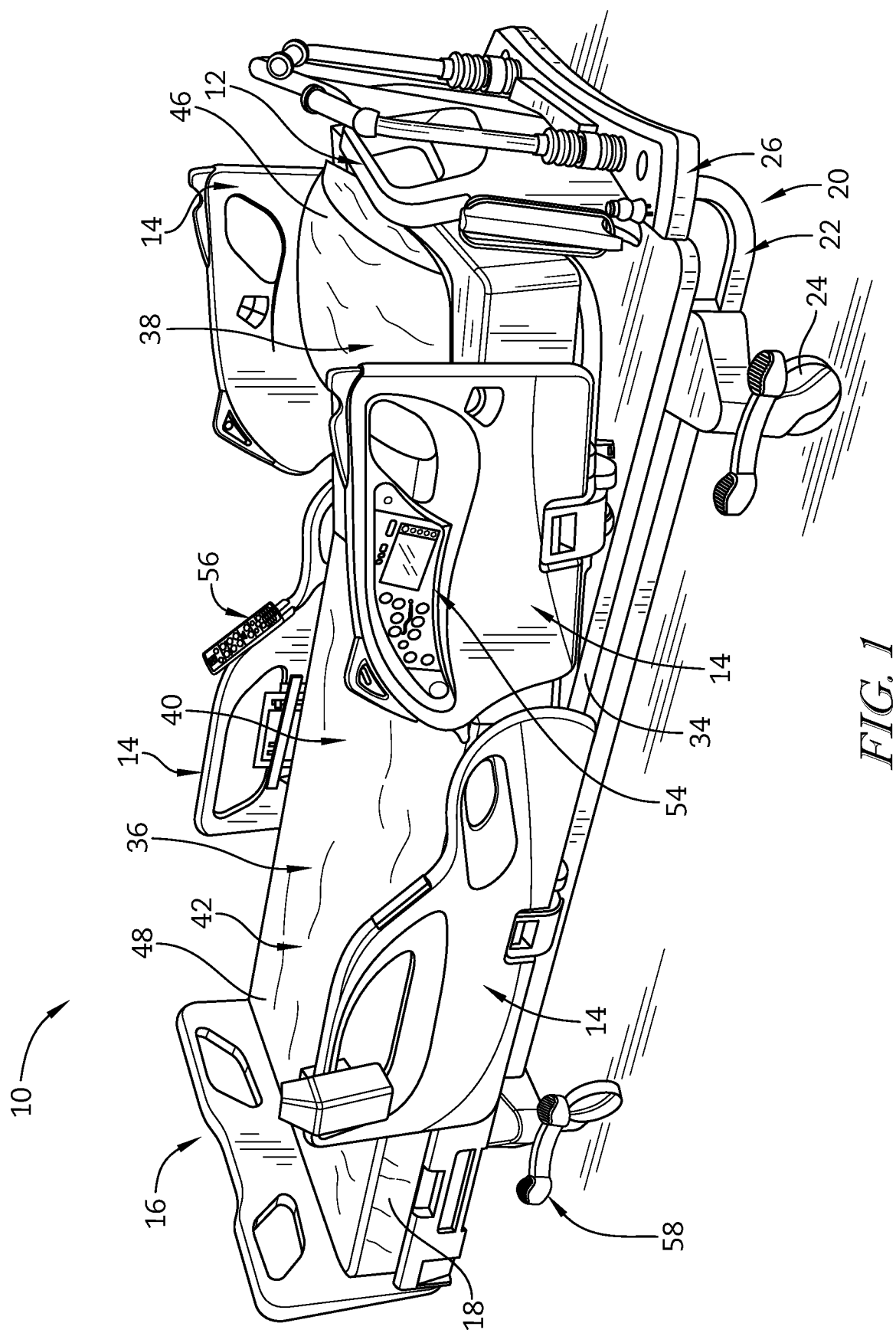
FIG. 1 is a perspective view from the foot end on the patient's right of a patient support apparatus.

An illustrative patient support apparatus 10 embodied as a hospital bed is shown in FIG. 1. The patient support apparatus 10 of FIG. 1 has a fixed bed frame 20 which includes a stationary base frame 22 with casters 24 and an upper frame 26. The stationary base frame 22 is further coupled to a weigh frame 30 that is mounted via frame member 32a and 32b to an adjustably positionable mattress support frame or deck 34 configured to support a mattress 18. The mattress 18 defines a patient support surface 36 which includes a head section 38, a seat section 40, and a foot section 42. The patient support apparatus 10 further includes a headboard 12 at a head end 46 of the patient support apparatus 10, a footboard 14 at a foot end 48 of the patient support apparatus 10, and a pair of siderails 16 coupled to the upper frame 26 of the patient support apparatus 10. The siderail 16 supports a patient monitoring control panel and/or a mattress position control panel 54. The patient support apparatus 10 is generally configured to adjustably position the mattress support frame 34 relative to the base frame 22.

Conventional structures and devices may be provided to adjustably position the mattress support frame 34, and such conventional structures and devices may include, for example, linkages, drives, and other movement members and devices coupled between base frame 22 and the weigh frame 30, and/or between weigh frame 30 and mattress support frame 34. Control of the position of the mattress support frame 34 and mattress 18 relative to the base frame 22 or weigh frame 30 is provided, for example, by a patient control pendant 56, a mattress position control panel 54, and/or a number of mattress positioning pedals 58. The mattress support frame 34 may, for example, be adjustably positioned in a general incline from the head end 46 to the foot end 48 or vice versa. Additionally, the mattress support frame 34 may be adjustably positioned such that the head section 38 of the patient support surface 36 is positioned between minimum and maximum incline angles, e.g., 0-65 degrees, relative to horizontal or bed flat, and the mattress support frame 34 may also be adjustably positioned such that the seat section 40 of the patient support surface 36 is positioned between minimum and maximum bend angles, e.g., 0-35 degrees, relative to horizontal or bed flat. Those skilled in the art will recognize that the mattress support frame 34 or portions thereof may be adjustably positioned in other orientations, and such other orientations are contemplated by this disclosure.

Figure 2:
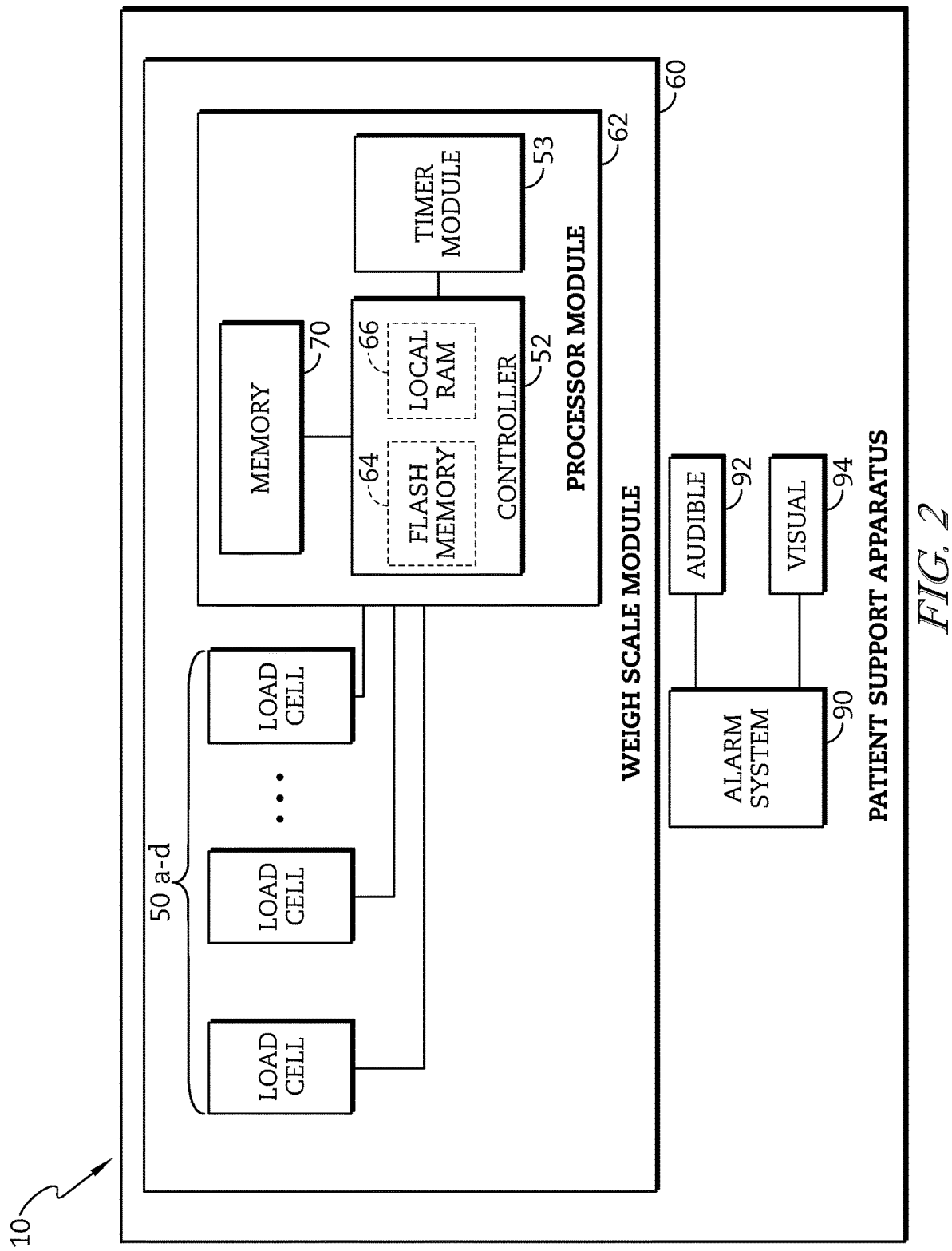
FIG. 2 is a block diagram of a portion of the electrical system of the patient support apparatus of FIG. 1 used to determine a tare weight of the patient support apparatus.

In one illustrative embodiment shown diagrammatically in FIG. 2, the patient support apparatus 10 includes a weigh scale module 60 and an alarm system 90. The weight scale module 60 is configured to determine a plurality set of calibration weights for each of a number of load cells 50 for use in determining a location and an accurate weight of the patient. To determine a weight of a patient supported on the patient support surface 36, the load cells 50 are positioned between the weigh frame 30 and the base frame 22. Each load cell 50 is configured to produce a voltage or current signal indicative of a weight supported by that load cell 50 from the weigh frame 30 relative to the base frame 22. The weigh scale module 60 includes a processor module 62 that is in communication with each of the respective load cells 50. The processor module 62 includes a microprocessor-based controller 52 having a flash memory unit 64 and a local random-access memory (RAM) unit 66. The local RAM unit 66 is utilized by the controller 52 to temporarily store information corresponding to features and functions provided by the patient support apparatus 10. The alarm system 90 is configured to trigger an alarm if the movement of the patient exceeds a predetermined threshold. The alarm may be an audible alarm 92 and/or a visual alarm 94. The visual alarm 94 may be positioned, for example, on the mattress position control panel 54 and/or the patient control pendant 56.

Figure 3:
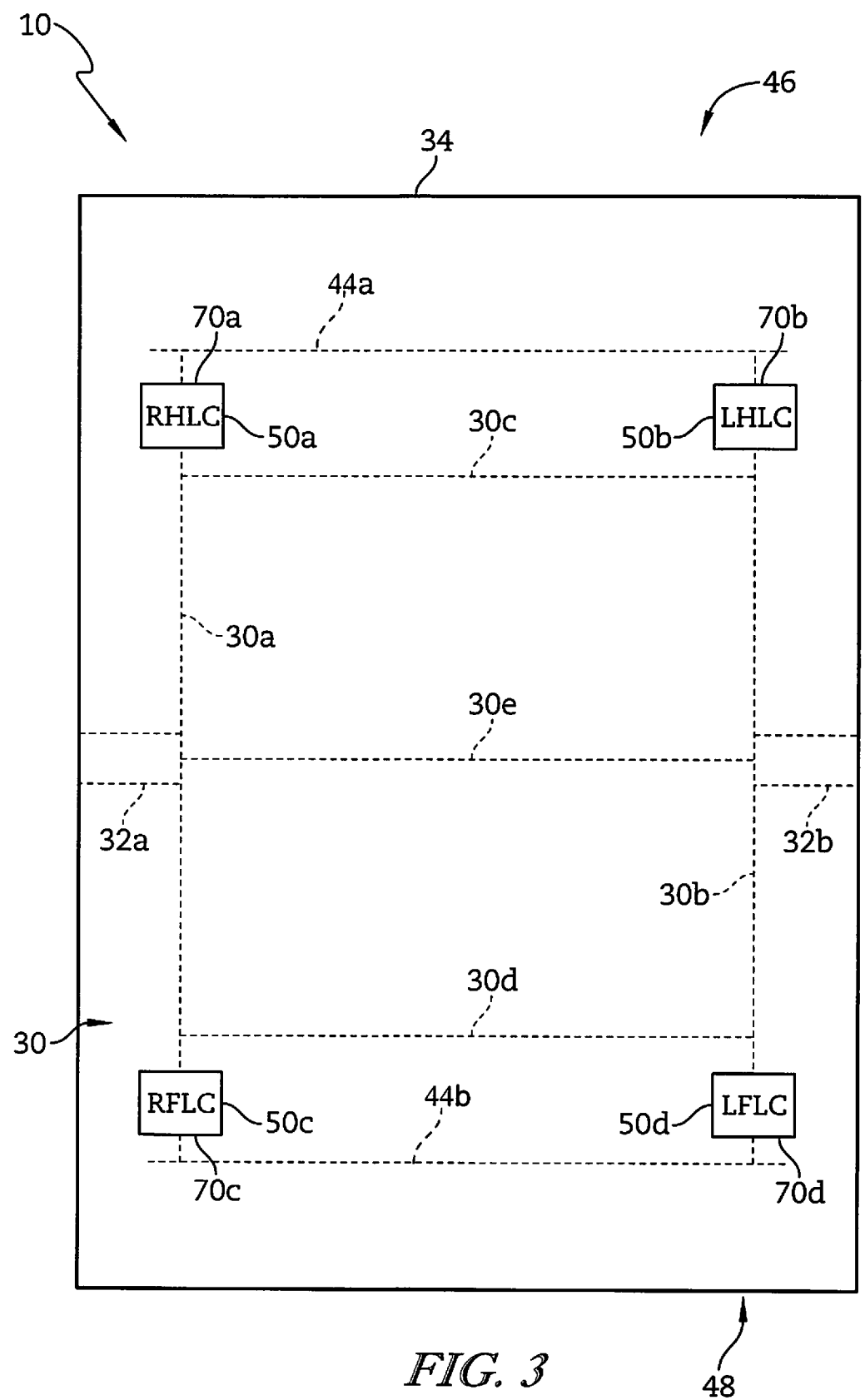
FIG. 3 is a diagrammatic representation of the positions of a number of load cells relative to the patient support apparatus of FIG. 1.

In the illustrated embodiment of FIG. 3, four such load cells 50a-50d are positioned between the weigh frame 30 and the base frame 22; one each near a different corner of the patient support apparatus 10. All four load cells 50a-50d are shown in FIG. 3. Some of the structural components of the patient support apparatus 10 will be designated hereinafter as "right", "left", "head" and "foot" from the reference point of an individual lying on the individual's back on the patient support surface 36 with the individual's head oriented toward the head end 46 of the patient support apparatus 10 and the individual's feet oriented toward the foot end 48 of the patient support apparatus 10. For example, the weigh frame 30 illustrated in FIG. 3 includes a head end frame member 30c mounted at one end to one end of a right side weigh frame member 30a and at an opposite end to one end of a left side frame member 30b. Opposite ends of the right side weigh frame member 30a and the left side weigh frame member 30b are mounted to a foot end frame member 30d. A middle weigh frame member 30e is mounted at opposite ends to the right and left side weigh frame members 30a and 30b respectively between the head end and foot end frame members 30c and 30d. The frame member 32a is shown mounted between the right side frame member 30a and the mattress support frame 34, and the frame member 32b is shown mounted between the left side frame member 30b and the mattress support frame 34. It will be understood that other structural support is provided between the weigh frame member 30 and the mattress support frame 34.

A right head load cell (RHLC) 50a is illustratively positioned near the right head end of the patient support apparatus 10 between a base support frame 44a secured to the base 44 near the head end 46 of the patient support apparatus 10 and the junction of the head end frame member 30c and the right side frame member 30a, as shown in the block diagram of FIG. 2. A left head load cell (LHLC) 50b is illustratively positioned near the left head end of the patient support apparatus 10 between the base support frame 44a and the junction of the head end frame member 30c and the left side frame member 30b, as shown in the block diagram of FIG. 3. A right foot load cell (RFLC) 50c is illustratively positioned near the right foot end of the patient support apparatus 10 between a base support frame 44b secured to the base 44 near the foot end 48 of the patient support apparatus 10 and the junction of the foot end frame member 30d and the right side frame member 30a, as shown in the block diagram of FIG. 3. A left foot load cell (LFLC) 50d is illustratively positioned near the left foot end of the patient support apparatus 10 between the base support frame 44b and the junction of the foot end frame member 30d and the left side frame member 30b. In the exemplary embodiment illustrated in FIG. 3, the four corners of the mattress support frame 34 are shown extending beyond the four corners of the weigh frame 30, and hence beyond the positions of the four load cells 50a-50d.

A weight distribution of a load among the plurality of load cells 50a-50d may not be the same depending on sensitivities of each of load cells 50a-50d and a position of the load on the patient support surface 36. Accordingly, a calibration constant for each of the load cells 50a-50d is established to adjust for differences in the load cells 50a-50d in response to the load. Each of the load cells 50a-50d produces a signal indicative of the load supported by that load cell 50. The loads detected by each of the respective load cells 50a-50d are adjusted using a corresponding calibration constant for the respective load cell 50a-50d. The adjusted loads are then combined to establish the actual weight supported on the patient support apparatus 10.

To determine a set of calibration constants, a calibration weight is sequentially placed on each of several predetermined calibration positions 70 on the patient support surface 36. For example, when determining a set of initial calibration constants, the calibration positions 70a, 70b, 70c, and 70d corresponding to the location of the load cells 50a, 50b, 50c, and 50d, respectively, are used. The calibration weight has an established mass which is used to determine the calibration constants. The respective initial calibration constants are determined by placing the calibration weight on a first calibration position 70a and measuring the weight distribution of the predefined calibration weight on each of the respective load cells 50a-50d. The respective loads detected by each of the load cells 50a-50d that corresponds to the current distribution of the predefined calibration weight on the first calibration position 70a is established and stored in memory 66. The predefined calibration weight is then moved to the next calibration position 70b and the measuring and storing steps are repeated until a set of load weights are established for each of the respective calibration positions 70a-70d.

The plurality sets of load weights that correspond to the location of each load cell 50a-50d are used to generate the calibration equations (1)-(4) set forth below.

$$CWRH = C_1L_1 + C_2L_2 + C_3L_3 + C_4L_4 \tag{1}$$

$$CWLH = C_1L_1 + C_2L_2 + C_3L_3 + C_4L_4 \tag{2}$$

$$CWRF = C_1L_1 + C_2L_2 + C_3L_3 + C_4L_4 \tag{3}$$

$$CWLF = C_1L_1 + C_2L_2 + C_3L_3 + C_4L_4 \tag{4}$$

where CWRH, CWRF, CWLF, and CWLH are the predefined calibration weight when the predefined calibration weight is positioned on the calibration positions 70a-70d which correspond to the RHLC 50a, RFLC 50b, LFLC 50c, and LHLC 50d, respectively, $C_1$, $C_2$, $C_3$, and $C_4$ are calibration constants for RHLC 50a, RFLC 50b, LFLC 50c, and LHLC 50d, respectively, and $L_1$, $L_2$, $L_3$, and $L_4$ are the load weights on RHLC 50a, RFLC 50b, LFLC 50c, and LHLC 50d, respectively. CWRH, CWRF, CWLF, and CWLH are all equal to the predefined calibration weight. Thus, the initial calibration constants $C_1$, $C_2$, $C_3$, and $C_4$ are established using a standard Gauss-Jordan or other appropriate elimination method and equations (1)-(4) are solved to obtain values for initial calibration constants $C_1$, $C_2$, $C_3$, and $C_4$. The initial calibration constants $C_1$, $C_2$, $C_3$, and $C_4$ are applied to the loads detected by the respective load cells 50a-50d is used to determine the total weight supported on the load cells 50a-50d. It should be appreciated that the calibration constants may be dynamically refined based on the position and/or weight of the load.

In some embodiments, the position of the patient is determined by calculating a locus of a centroid of the patient load. The centroid of the patient load is represented as a point relative to a reference position or a coordinate axis of the patient support apparatus 10. The point is a coordinate (X, Y) within a two-dimensional Cartesian coordinate system having two horizontally extending X and Y axes along the patient support surface 36. The determination of the centroid of the patient load is described in expired U.S. Pat. No. 5,276,432, which is incorporated by reference herein in its entirety.

Figure 4:
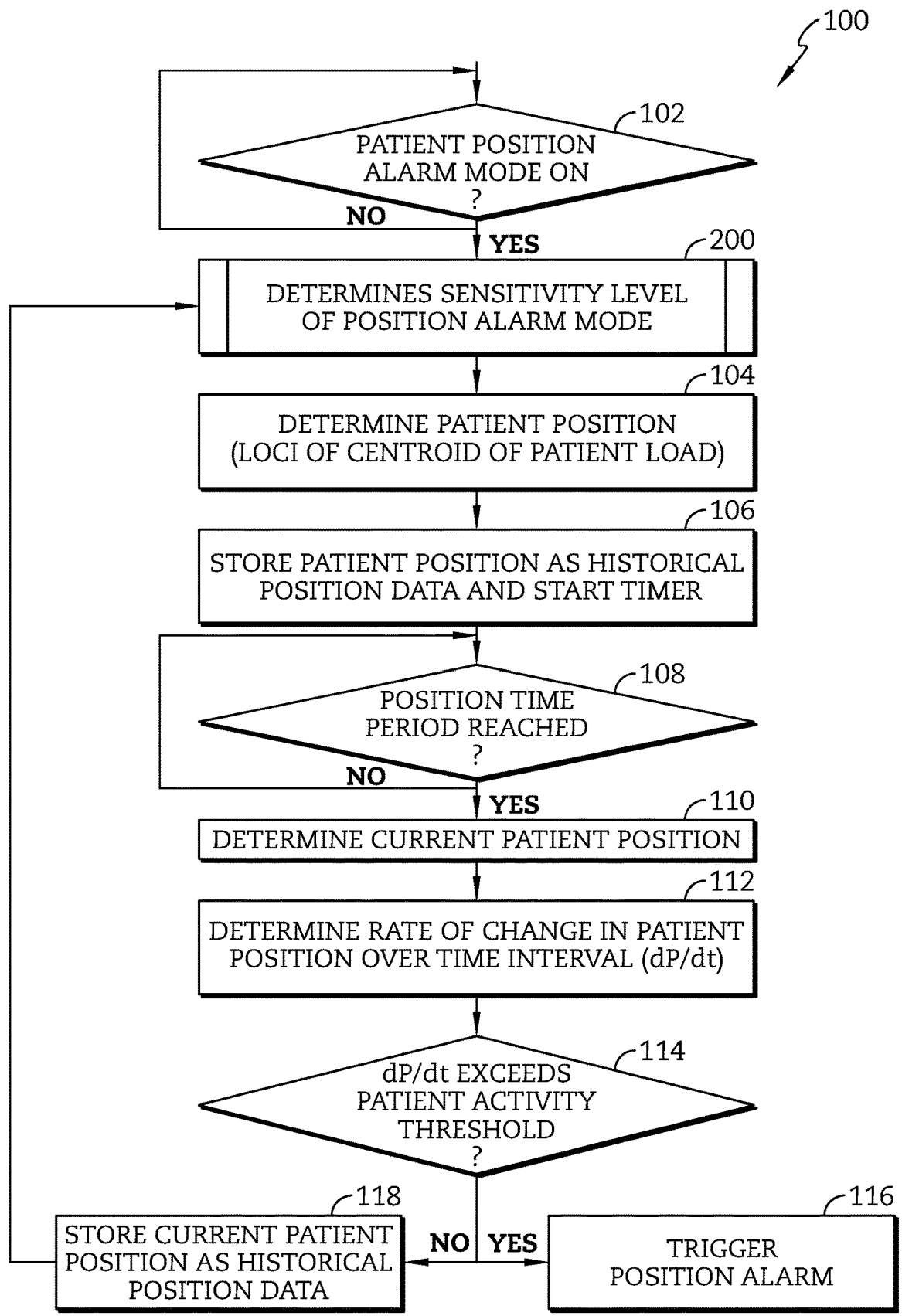
FIG. 4 is a flowchart illustrating an exemplary embodiment of a software routine for executing a patient position alarm mode for determining a patient weight.
Figure 5:
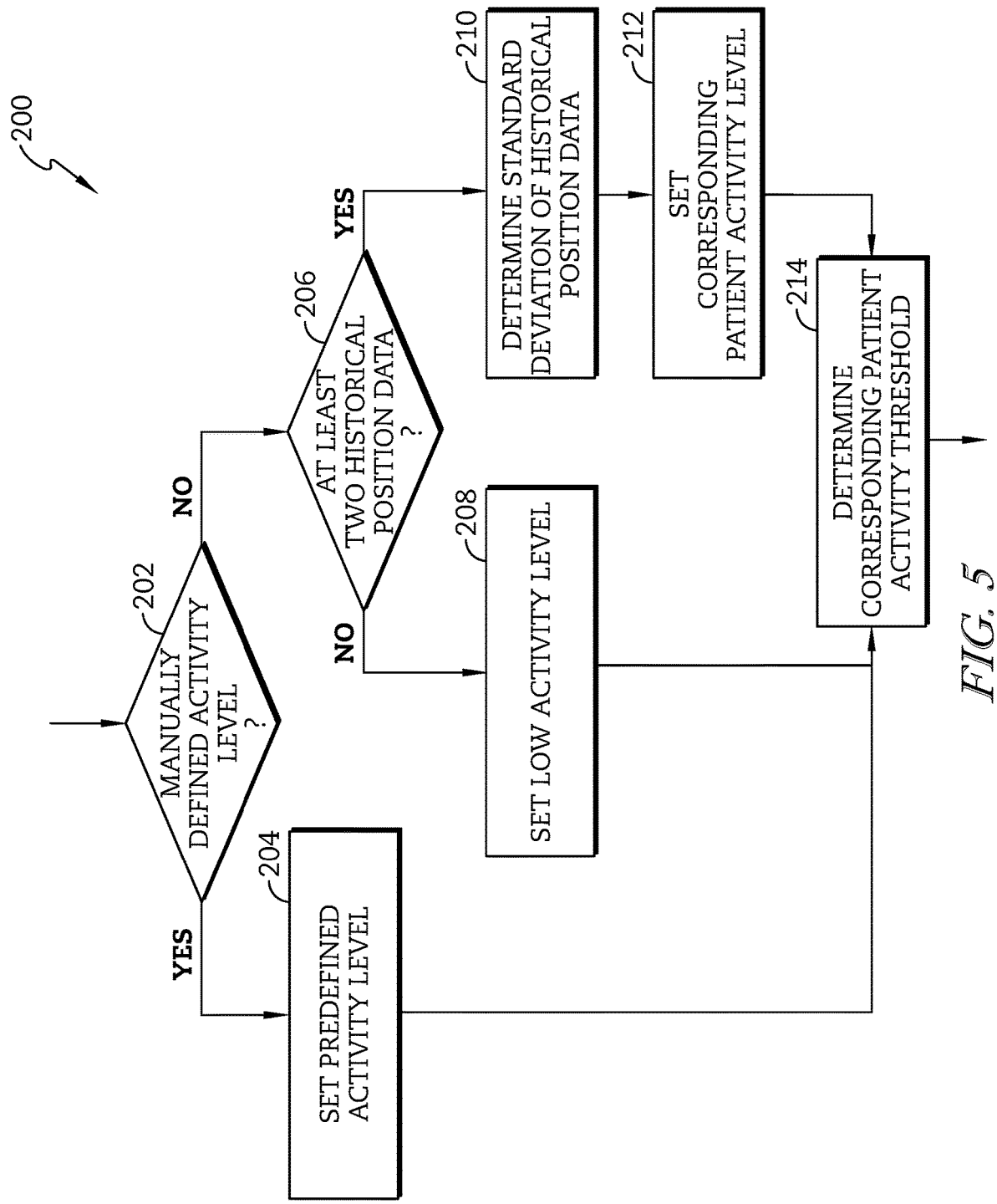
FIG. 5 is a flow chart showing a sub-routine process for determining a patient activity level supported on the patient support apparatus that forms one part of the process of FIG. 4.
Figure 6:
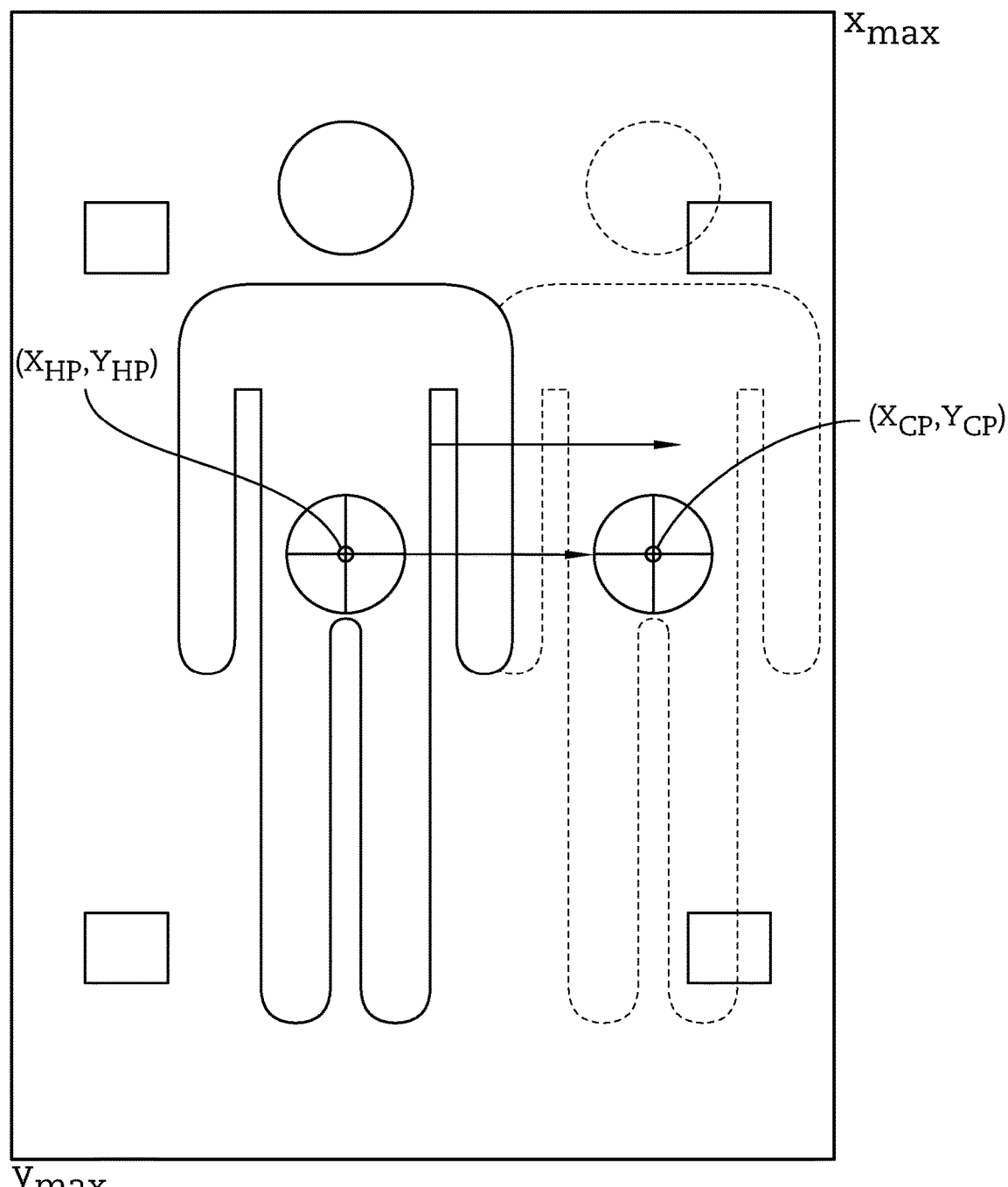
FIG. 6 is a diagrammatic representation similar to FIG. 3 of the position of a patient supported on the patient support apparatus.

In one illustrative embodiment shown in FIGS. 4-6, the patient support apparatus 10 includes a weigh scale module 160 configured to detect a patient position by determining the patient movement on the patient support surface 36 of the patient support apparatus 10. As shown in FIG. 4, a patient position alarm process 100 determines the rate of change in patient position on the patient support surface 36 and triggers the alarm if the rate exceeds a predetermined threshold. As discussed previously, the alarm may be an audible and/or visual. The process 100 illustratively begins at decision step 102 where the controller 52 is operable to determine whether the patient position alarm mode is on. If the controller 52 determines that the patient position alarm mode is on, the process 100 advances to step 200. At step 200, the controller 52 determines a sensitivity level of the position alarm mode. The sensitivity of the position alarm mode routine depends upon an activity level of the patient supported on the patient support apparatus 10. The patient activity level is illustratively high, moderate, or low but could be any of a number of different levels. Each patient activity level has a different position alarm threshold. For example, the patient with high activity level has an active patient threshold; the patient with moderate activity level has an intermediate patient threshold; and the patient with low activity level has a sedentary patient threshold. In addition, the patient activity level may be fixed or dynamic during the patient position alarm process 100.

Generally, depending on the health of the patient, a caregiver may predetermine the patient activity level and manually record it in the memory 66 prior to executing the patient position alarm mode. At step 202, the controller 52 determines whether the patient activity level was manually defined by the user. If the controller 52 determines that the patient activity level is predefined, the process 200 proceeds to step 204 to set the predefined activity level. If, however, the controller 52 determines that the activity level was not manually defined, the process 200 proceeds to step 206. At step 206, the controller 52 determines whether there are at least two historical position data points in the memory 66. If the controller 52 determines that there are less than two historical position data points in the memory 66, the controller 52 sets the sensitivity level of the position alarm mode to correspond to the low activity level. If the controller 52 determines that there are at least two historical position data, the process 200 proceeds to step 210. At step 210, the controller 52 determines a standard deviation of a subset of all of the available historical position data. It should be appreciated that the controller 52 may take "n" number of latest historical position data to determine the standard deviation. In other words, the standard deviation changes depending on the recent activities of the patient supported on the patient support apparatus 10. Subsequent to determining the standard deviation, the controller 52 determines the corresponding patient activity level. Once the patient activity level is set at step 204, 208, 212, the process 200 proceeds to step 214, where the controller 52 determines the patient activity threshold corresponding to the patient activity level. The process 200 then proceeds to step 104 of the process 100.

At step 104, the controller 52 determines the position of the patient on the patient support surface 36. The position of the patient is determined by calculating the centroid of the patient load as a coordinate in x-axis and y-axis of the patient support surface 36 as shown in FIG. 6. Once the locus of the centroid of the patient load of the patient is determined, the controller 52 stores the coordinate as a function of historical position data ($X_{HP}$, $Y_{HP}$). After storing the position at step 106, the controller 52 starts a timer and proceeds to decision step 108. At step 108, the controller 52 determines whether a predefined position time period is reached. If the controller 52 determines that the position time period is reached, the process 100 advances to step 110. At step 110, the controller 52 again determines the current patient position by calculating the location of the center of the gravity of the patient. Then, the controller 52 determines the rate of change in patient position as a function of time (dP/dt), where dP is the change in distance between the historical position data ($X_{HP}$, $Y_{HP}$) and dt is the corresponding time period. The change in distance (dP) between the historical position data ($X_{HP}$, $Y_{HP}$) and the current position data ($X_{CP}$, $Y_{CP}$)) is calculated by applying equation (5).

$$dP=\sqrt{|(X_{HP}-X_{CP})|^2+|(Y_{HP}-Y_{CP})|^2} \qquad (5)$$

Once the rate of change in patient position (dP/dt) is determined, the process 100 advances to step 114, where the controller 52 determines whether the rate of change in patient position (dP/dt) exceeds the patient activity threshold which was determined at step 200. For example, if the controller 52 determines, at step 200, that the patient supported on the patient support apparatus 10 is an active patient, the controller 52 determines whether the rate of change in patient position (dP/dt) exceeds the active patient threshold. If the controller 52 determines that the rate of change in patient position (dP/dt) exceeds the established patient activity threshold, the process 100 proceeds to step 116 where the controller 52 triggers an alarm.

If, however, the controller 52 determines that the rate of change in patient position (dP/dt) does not exceed the patient activity threshold, the process 100 proceeds to step 118 where the controller 52 stores the current patient position ($X_{CP}$, $Y_{CP}$)) as a function of historical position data ($X_{HP}$, $Y_{HP}$). The process 100 then proceeds back to step 200 where the controller 52 updates the sensitivity level of the position alarm mode routine based on the historical position data, including the latest historical position data.

Figure 7:
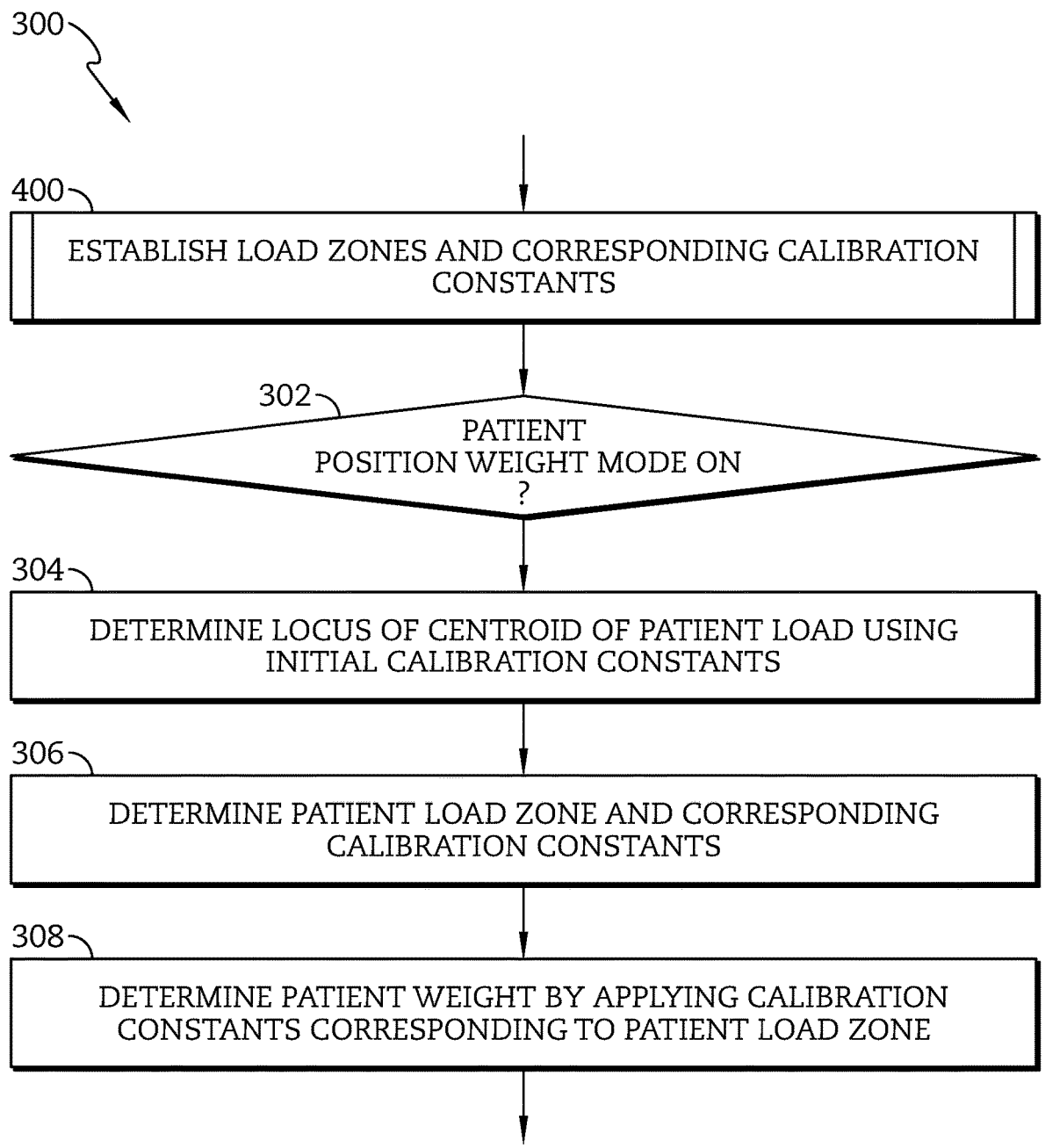
FIG. 7 is a flowchart illustrating an exemplary embodiment of a software routine for executing a patient position weight mode for determining the patient weight.
Figure 8:
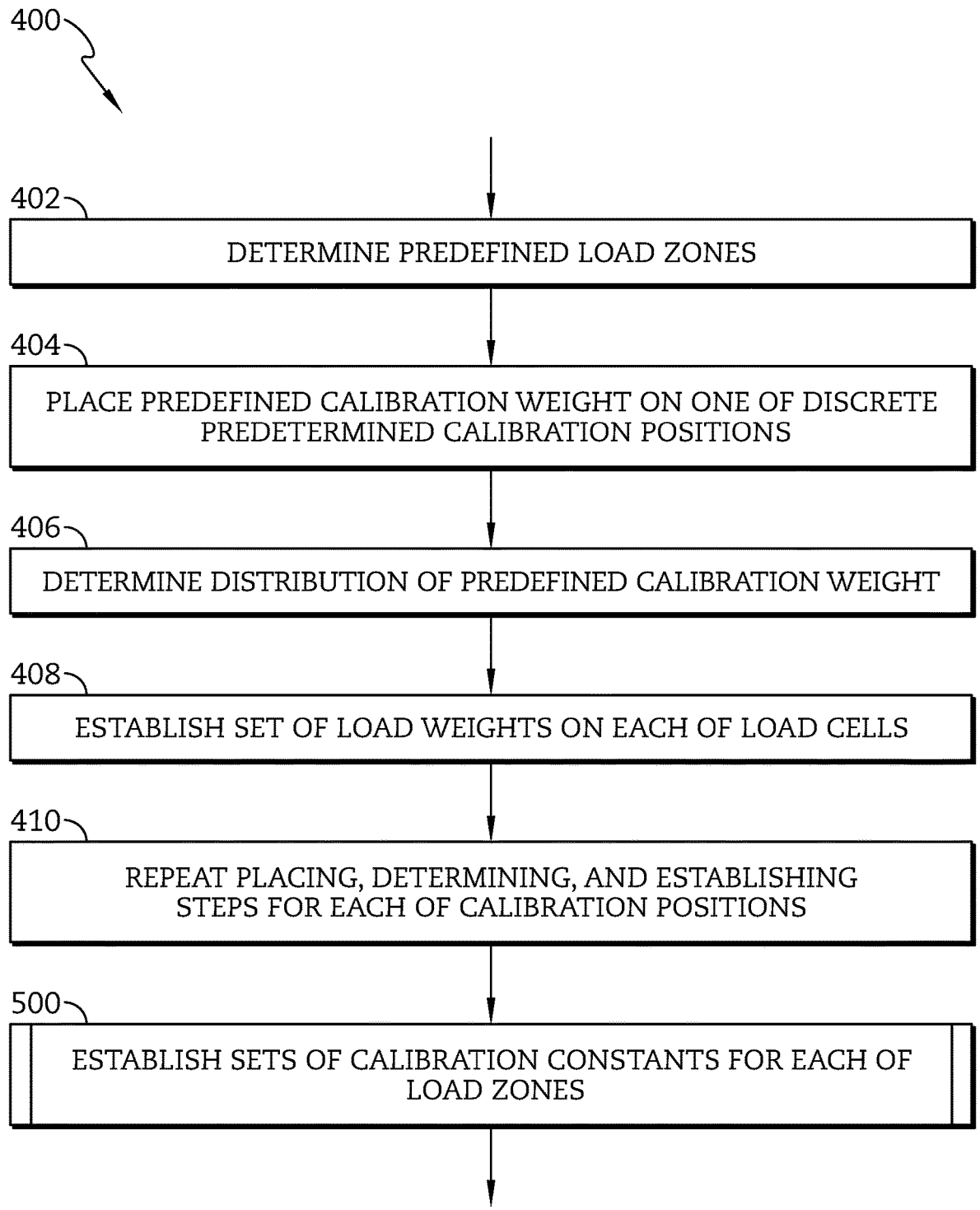
FIG. 8 is a flow chart showing a sub-routine process establishing load zones and its corresponding set of calibration constants that forms one part of the process of FIG. 7.
Figure 9:
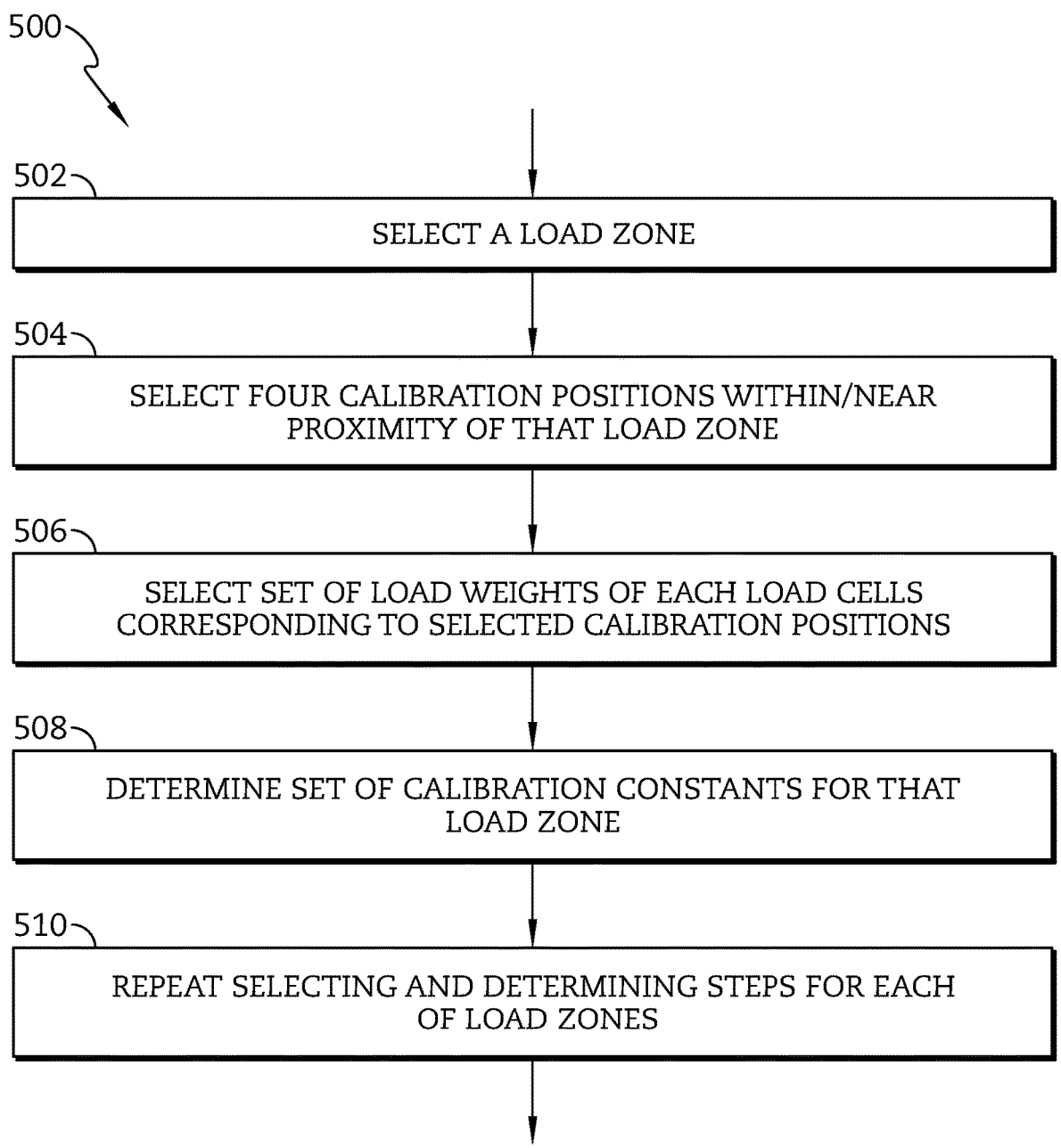
FIG. 9 is a flow chart showing a sub-routine process establishing sets of calibration constants for each load zones that forms one part of the process of FIG. 8.
Figure 10:
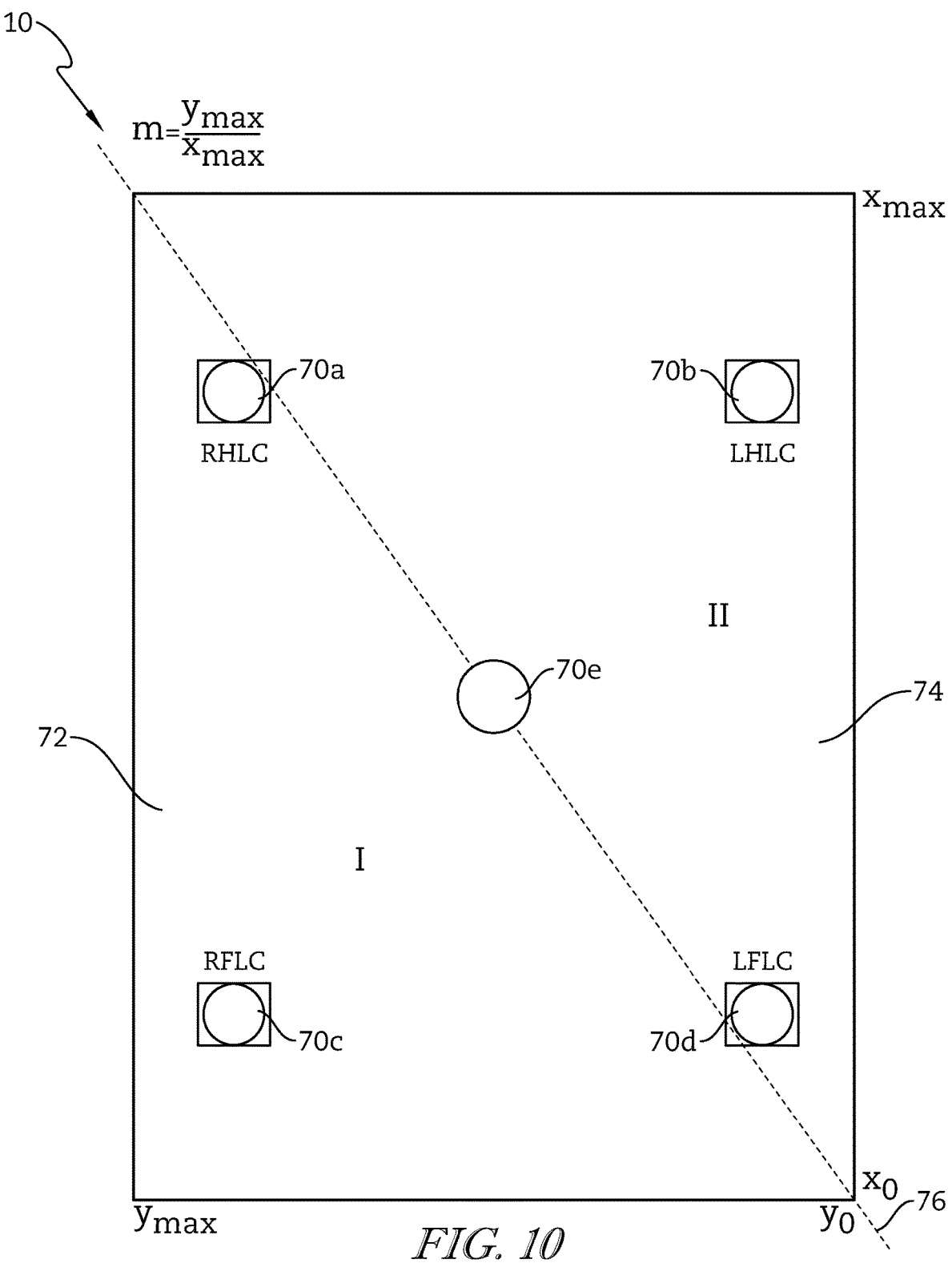
FIG. 10 is a top plan view of a first embodiment of a patient support apparatus of FIG. 1 with two load zones.
Figure 11:
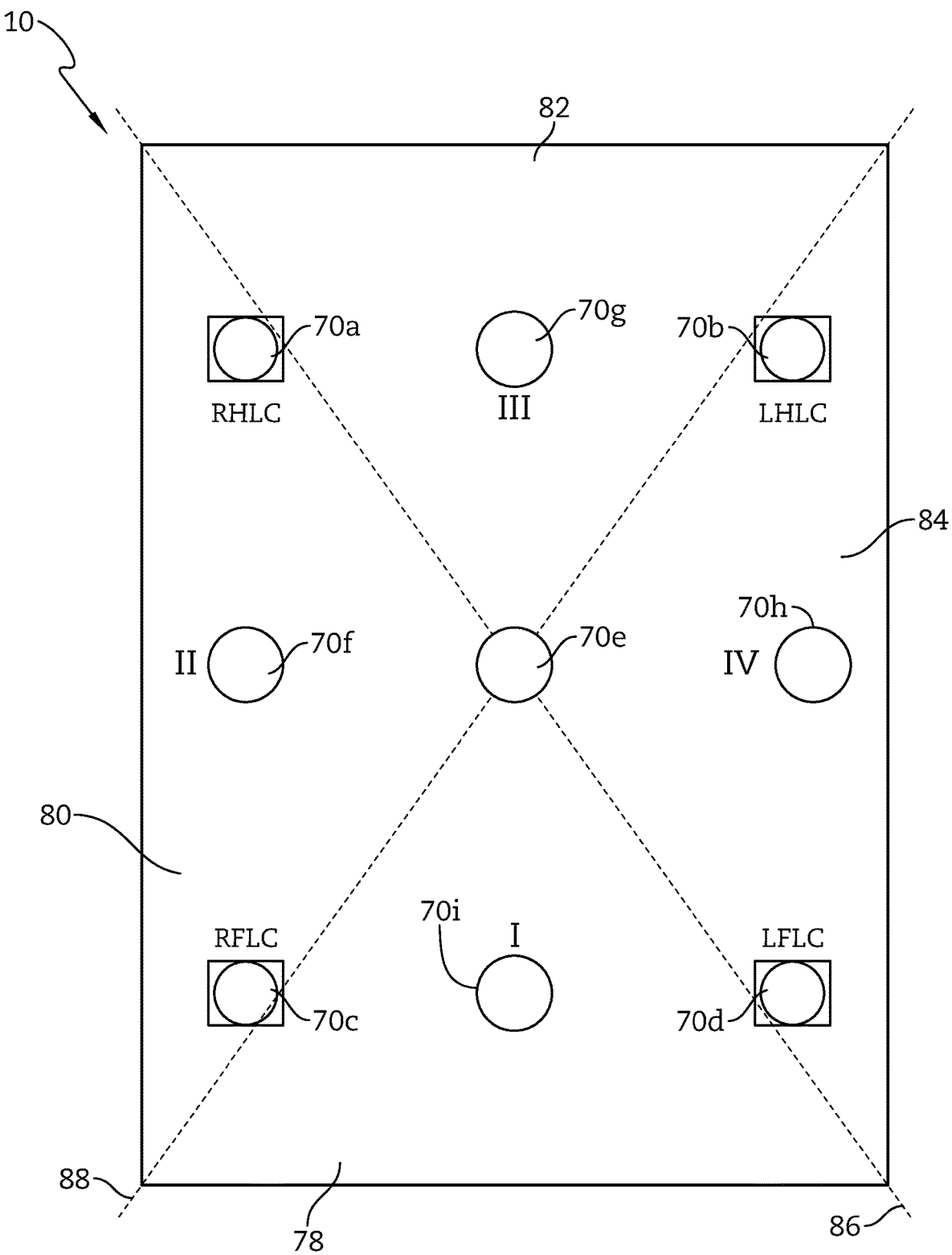
FIG. 11 is a top plan view of a second embodiment of a patient support apparatus of FIG. 1 with four load zones.

In another illustrative embodiment shown in FIGS. 7-10, the patient support apparatus 10 includes a weigh scale module 260 configured to determine the weight of the patient. As shown in FIG. 7, a patient position weight process 300 determines the patient weight by determining the patient position. The process 300 illustratively begins at step 400 where the controller 52 is operable to establish load zones and calibration constants that vary depending on which zone the centroid of the load is positioned. The load zones are areas defined on the patient support surface 36 and a number of load zones may vary. Some examples of the patient support apparatus 10 with different load zones are shown in FIGS. 10-11. For example, as shown in FIG. 10, the patient support apparatus 10 may be divided into two load zones 72, 74. The load zones 72, 74 are divided by a diagonal line 76 extending from the patient's right head end of the patient support apparatus 10 to the patient's left foot end of the apparatus 10. However, it may extend from the patient's left head end to the patient's right foot end. In another example, as shown in FIG. 11, the patient support apparatus 10 may be divided into four load zones 78, 80, 82, 84. The load zones 78, 80, 82, 84 are divided by two diagonal lines 86, 88, a first line extending from the patient's right head end to the patient's left foot end, and a second line extending from the patient's left head end to the patient's right foot end.

At step 402, the process 400 determines the predefined number of load zones and proceeds to decision step 404. At step 404, an object with a predefined calibration weight is placed on one of a plurality of calibration positions 70. The plurality of the calibration positions 70 varies depending on the number of load zones. For example, as shown in FIG. 10, the patient support surface 36 may have two load zones 72, 74 defined by five calibration positions 70a-70e such that load zone I is defined by the calibration positions 70a, 70c, 70d, and 70e and load zone II is defined by the calibration positions 70a, 70b, 70d, and 70e. For such an embodiment, the object with the predefined calibration weight is placed on a first calibration position 70a and the weight distribution of the predefined calibration weight on each of the respective load cells 50a-50b is determined. Then a set of load weights $L_1$, $L_2$, $L_3$, and $L_4$ for each of the respective load cells 50a-50d that corresponds to the current distribution of the predefined calibration weight at the first calibration position 70a is established and stored in memory 66. The predefined calibration weight is then moved to the next calibration position 70b and the measuring and storing steps are repeated until all a set of load weights are established for each of the load cells 50a-50d. The plurality sets of load weights that correspond to each calibration position 70 are used to generate the calibration equations (6)-(10) set forth below.

$$CW_a = C_1 L_1 + C_2 L_2 + C_3 L_3 + C_4 L_4 \quad (6)$$

$$CW_b = C_1 L_1 + C_2 L_2 + C_3 L_3 + C_4 L_4 \quad (7)$$

$$CW_c = C_1 L_1 + C_2 L_2 + C_3 L_3 + C_4 L_4 \quad (8)$$

$$CW_d = C_1 L_1 + C_2 L_2 + C_3 L_3 + C_4 L_4 \quad (9)$$

$$CW_e = C_1 L_1 + C_2 L_2 + C_3 L_3 + C_4 L_4 \quad (10)$$

where $CW_a$, $CW_b$, $CW_c$, $CW_d$, and $CW_e$ are the predefined calibration weight when the predefined calibration weight is placed on the calibration position 70a, 70b, 70c, 70d, and 70e, respectively, $C_1$, $C_2$, $C_3$, and $C_4$ are calibration constants for RHLC 50a, RFLC 50c, LFLC 50d, and LHLC 50b, respectively, and $L_1$, $L_2$, $L_3$, and $L_4$ are the load weights on RHLC 50a, RFLC 50c, LFLC 50d, and LHLC 50b, respectively. $CW_a$, $CW_b$, $CW_c$, $CW_d$, and $CW_e$ are all equal to the predefined calibration weight.

Once the process 400 determines the sets of load weights on each load cell for every load zones, the process 400 advances to step 500. At step 500, the controller 52 selects a load zone. As discussed previously, different load zones may invoke different calibration constants. For load zone I, the controller 52 uses the calibration equations from the calibration positions 70a, 70c, 70d, and 70e. Accordingly, the initial calibration constants are established using a standard Gauss-Jordan or other appropriate elimination method and equations (6), (8), (9), and (10) are solved to obtain values for calibration constants $C_{I-1}$, $C_{I-2}$, $C_{I-3}$, and $C_{I-4}$ for load zone I. For load zone II, the controller 52 uses the calibration equations from the calibration positions 70a, 70b, 70d, and 70e. Accordingly, the initial calibration constants are established using a standard Gauss-Jordan or other appropriate elimination method and equations (6), (7), (9), and (10) are solved to obtain values for calibration constants $C_{II-1}$, $C_{II-2}$, $C_{II-3}$, and $C_{II-4}$ for load zone II.

In some embodiments, as shown in FIG. 11, the patient support surface 36 may have four load zones 78, 80, 82, 84 defined by nine calibration positions 70a-70i. For such an embodiment, additional calibration positions 70 are defined between calibration position 70a and 70b, 70b and 70d, 70c and 70d, and 70a and 70c. Load zone I is defined by the calibration positions 70c, 70e, 70d, and 70i, load zone II is defined by the calibration position 70c, 70e, 70a, and 70f, load zone III is defined by the calibration position 70a, 70e, 70b, and 70g, and load zone IV is defined by the calibration position 70b, 70e, 70d, and 70h. The plurality sets of load weights that correspond to each calibration position 70 are used to generate the calibration equations (11)-(19) set forth below.

$$CW_a = C_1 L_1 + C_2 L_2 + C_3 L_3 + C_4 L_4 \quad (11)$$

$$CW_b = C_1 L_1 + C_2 L_2 + C_3 L_3 + C_4 L_4 \quad (12)$$

$$CW_c = C_1 L_1 + C_2 L_2 + C_3 L_3 + C_4 L_4 \quad (13)$$

$$CW_d = C_1 L_1 + C_2 L_2 + C_3 L_3 + C_4 L_4 \quad (14)$$

$$CW_e = C_1 L_1 + C_2 L_2 + C_3 L_3 + C_4 L_4 \quad (15)$$

$$CW_f = C_1 L_1 + C_2 L_2 + C_3 L_3 + C_4 L_4 \quad (16)$$

$$CW_g = C_1 L_1 + C_2 L_2 + C_3 L_3 + C_4 L_4 \quad (17)$$

$$CW_h = C_1 L_1 + C_2 L_2 + C_3 L_3 + C_4 L_4 \quad (18)$$

$$CW_i = C_1 L_1 + C_2 L_2 + C_3 L_3 + C_4 L_4 \quad (19)$$

where $CW_a$, $CW_b$, $CW_c$, $CW_d$, $CW_e$, $CW_f$, $CW_g$, $CW_h$, and $CW_i$ are the predefined calibration weight when the predefined calibration weight is placed on the calibration position 70a, 70b, 70c, 70d, and 70e, respectively, $C_1$, $C_2$, $C_3$, and $C_4$ are calibration constants for RHLC 50a, RFLC 50c, LFLC 50d, and LHLC 50b, respectively, and $L_1$, $L_2$, $L_3$, and $L_4$ are the load weights on RHLC 50a, RFLC 50c, LFLC 50d, and LHLC 50b, respectively. $CW_a$, $CW_b$, $CW_c$, $CW_d$, $CW_e$, $CW_f$, $CW_g$, $CW_h$, and $CW_i$ are all equal to the predefined calibration weight.

For each load zone, the controller 52 uses the calibration equations from the calibration positions 70 that are within or in proximity of that load zone. For load zone I, the controller 52 uses the calibration equations from the calibration positions 70c, 70e, 70d, and 70i. Accordingly, the initial calibration constants are established using a standard Gauss-Jordan or other appropriate elimination method and equations (13), (15), (14), and (19) are solved to obtain values for calibration constants $C_{I-1}$, $C_{I-2}$, $C_{I-3}$, and $C_{I-4}$ for load zone I. For load zone II, the controller 52 uses the calibration equations from the calibration position 70c, 70e, 70a, and 70f. Accordingly, the initial calibration constants are established using a standard Gauss-Jordan or other appropriate elimination method and equations (13), (15), (11), and (16) are solved to obtain values for calibration constants $C_{II-1}$, $C_{II-2}$, $C_{II-3}$, and $C_{II-4}$ for load zone II. For load zone III, the controller 52 uses the calibration equations from the calibration position 70a, 70e, 70b, and 70g. Accordingly, the initial calibration constants are established using a standard Gauss-Jordan or other appropriate elimination method and equations (11), (15), (12), and (17) are solved to obtain values for calibration constants $C_{III-1}$, $C_{III-2}$, $C_{III-3}$, and $C_{III-4}$ for load zone III. For load zone IV, the controller 52 uses the calibration equations from the calibration position 70b, 70e, 70d, and 70h. Accordingly, the initial calibration constants are established using a standard Gauss-Jordan or other appropriate elimination method and equations (12), (15), (14), and (18) are solved to obtain values for calibration constants $C_{IV-1}$, $C_{IV-2}$, $C_{IV-3}$, and $C_{IV-4}$ for load zone IV.

Once the load zones and the corresponding calibration constants for each load cell 50a-50d are established, the process 400 proceeds to decision step 302. At step 302, the controller 52 determines whether a patient position weight mode is on. If the controller 52 determines that the patient position weight mode is on, the process 300 advances to step 304. At step 304, the controller 52 determines the locus ($x_1$, $y_1$) of centroid of patient load using the set of initial calibration constants for each load cell 50. The process 300 then proceeds to step 306 where the controller 52 determines the load zone that contains the locus of the centroid of the patient load. As previously described, the controller 52 established the load zones on the patient support surface 36 at step 400. In one embodiment shown in FIG. 10, the controller 52 established that the patient support surface 36 has two load zones: zone I and zone II. The controller 52 determines whether the locus ($x_1$, $y_1$) falls within the zone I or zone II. The locus ($x_1$, $y_1$) falls within the zone I if $$\frac{y_1 - y_0}{x_1 - x_0} > \frac{y_{max}}{x_{max}},$$

and locus ($x_1$, $y_1$) falls within the zone II if $$\frac{y_1 - y_0}{x_1 - x_0} < \frac{y_{max}}{x_{max}}.$$

In another embodiment shown in FIG. 11, the controller 52 established that the patient support surface 36 has four load zones: zone I, zone II, zone III, and zone IV. The locus ($x_1$, $y_1$) falls within the zone I if $$\frac{y_1 - y_0}{x_1 - x_0} > \frac{y_{max}}{x_{max}} \text{ and } \frac{x_1 - x_0}{y_1 - y_0} < \frac{x_{max}}{y_{max}}.$$

The locus ($x_1$, $y_1$) falls within the zone II if $$\frac{y_1 - y_0}{x_1 - x_0} > \frac{y_{max}}{x_{max}} \text{ and } \frac{x_1 - x_0}{y_1 - y_0} > \frac{x_{max}}{y_{max}}.$$

The locus ($x_1$, $y_1$) falls within the zone III if $$\frac{y_1 - y_0}{x_1 - x_0} < \frac{y_{max}}{x_{max}} \text{ and } \frac{x_1 - x_0}{y_1 - y_0} < \frac{x_{max}}{y_{max}}.$$

The locus ($x_1$, $y_1$) falls within the zone IV if $$\frac{y_1 - y_0}{x_1 - x_0} < \frac{y_{max}}{x_{max}} \text{ and } \frac{x_1 - x_0}{y_1 - y_0} > \frac{x_{max}}{y_{max}}.$$

Once the patient load zone that corresponds to the locus ($x_1$, $y_1$) of centroid of patient load is determined, the controller 52 retrieves the set of calibration constants for that patient load zone which was determined at step 400 and the process 300 advances to step 308. At step 308, the controller 52 determines a total weight by using the set of calibration constants corresponding to the patient load zone.

Figure 12:
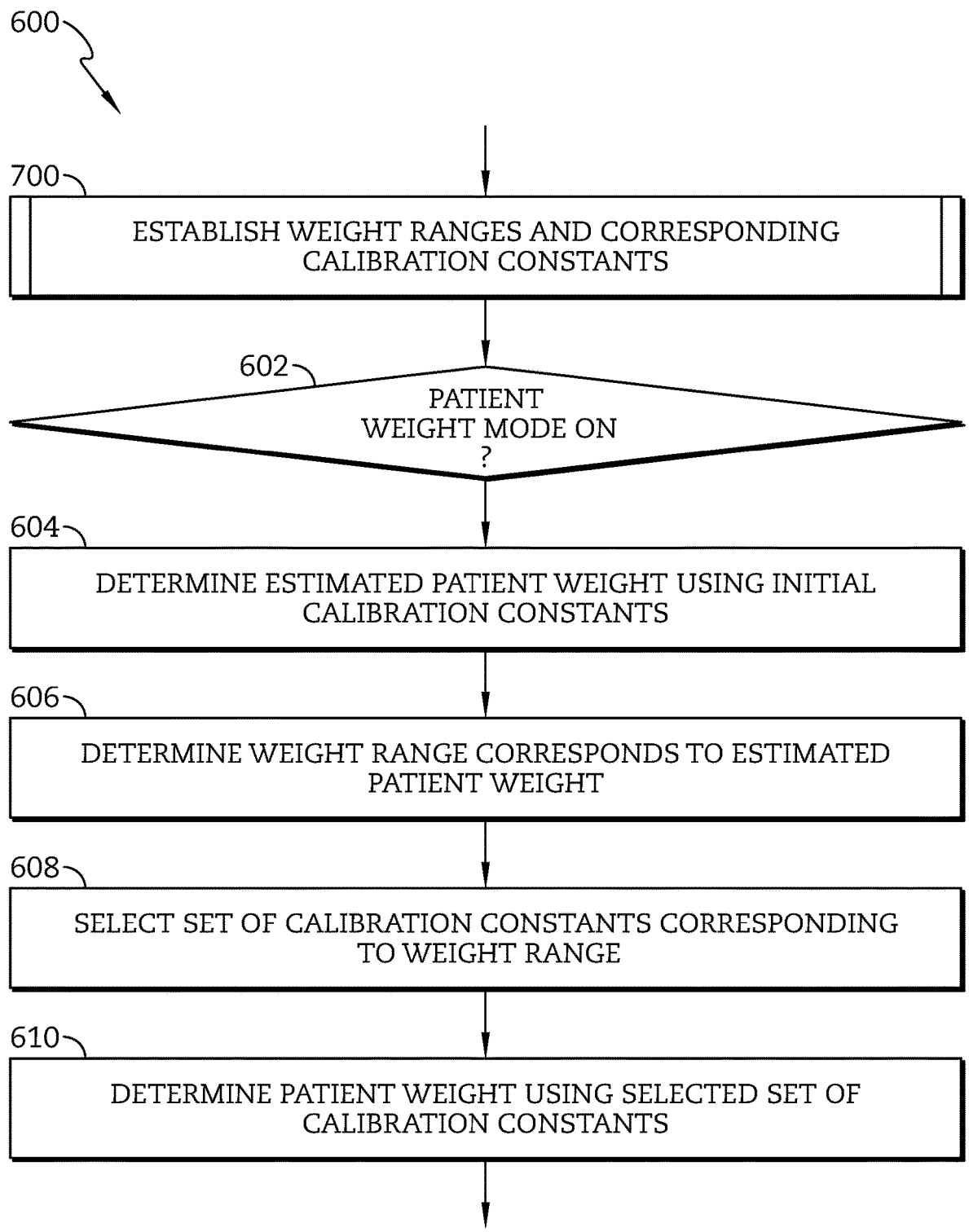
FIG. 12 is a flowchart illustrating an exemplary embodiment of a software routine for executing a patient weight mode for determining the patient weight.
Figure 13:
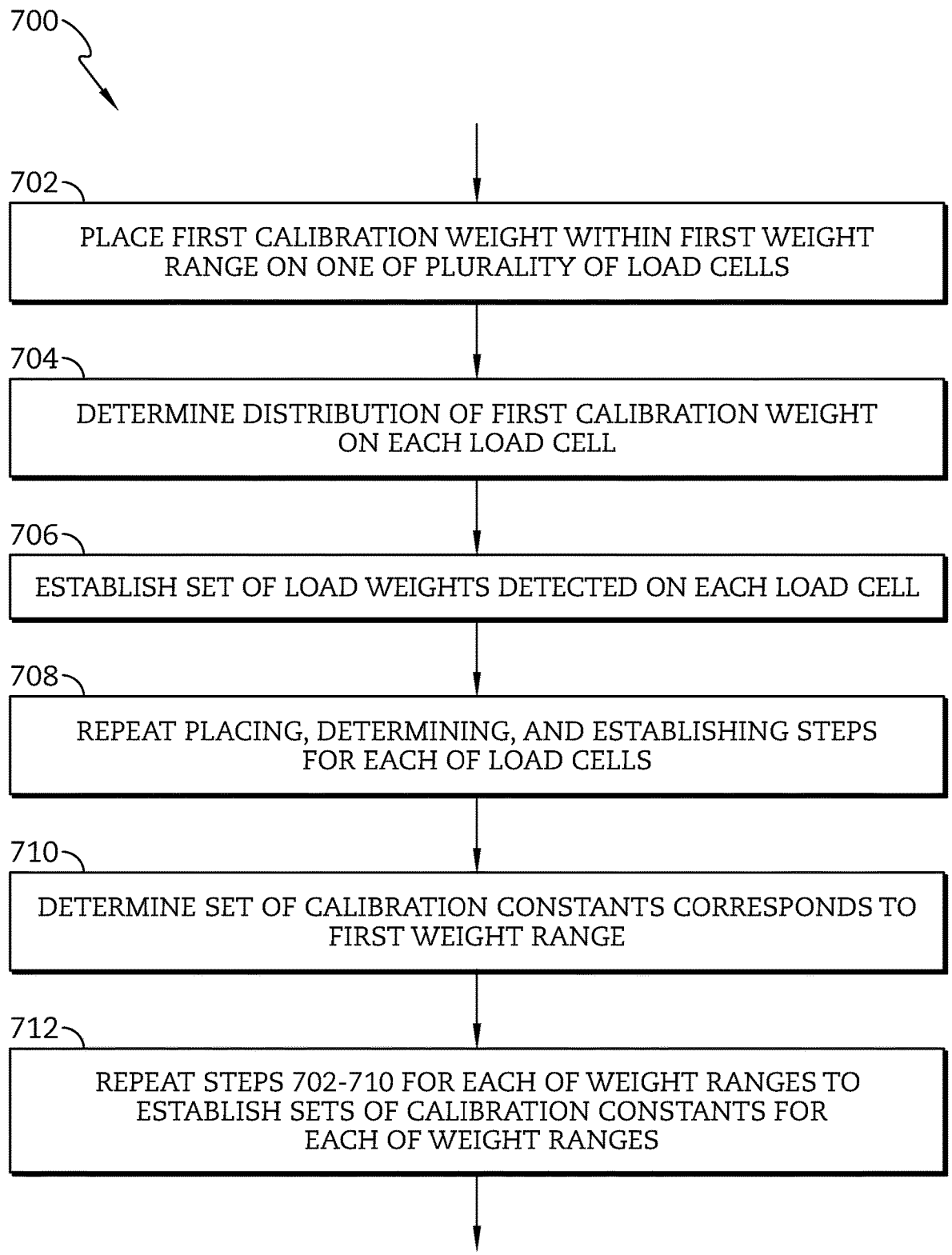
FIG. 13 is a flow chart showing a sub-routine process establishing calibration ranges and its corresponding set of calibration constants that forms one part of the process of FIG. 12.

In another illustrative embodiment shown in FIGS. 12-13, the patient support apparatus 10 includes a weigh scale module 360 configured to determine the accurate weight of the patient by determining a set of calibration constants that corresponds to a patient's weight. As discussed previously, weight distribution on multiple load cells is not equal at each load cell and other factors may affect weight distribution on the load cells, including a patient's weight. Since different weights may impose different weight distributions and different mechanical responses from the load cells 50a-50d, the weight scale module 360 applies a different set of calibration constants depending on the weight of the patient supported on the patient support apparatus 10.

As shown in FIG. 12, a patient weight process 600 illustratively begins at step 700 where the controller 52 is operable to establish weight ranges and a set of calibration constants for each weight range, which is shown in detail in FIG. 13. The weight ranges are ranges of possible patient weight supported on the patient support apparatus 10. For example, the patient weight can vary between 0 to 500 pounds and the weight ranges are in the increments of 50 pounds, such that there are Range 1 (0-50 pounds), Range 2 (51-100 pounds), Range 3 (101-150 pounds), Range 4 (151-200 pounds), Range 5 (201-250 pounds), Range 6 (251-300 pounds), Range 7 (301-350 pounds), Range 8 (351-400 pounds), Range 9 (401-450 pounds), and Range 10 (451-500 pounds). Each of these weight ranges may have a different set of calibration weights due to inconsistent sensitivities and mechanical responses from each of the load cells 50a-50d at different weight ranges.

At step 702, a first calibration weight within a first weight range is placed on one of the plurality of load cells. For example, the first calibration weight is 25 pounds, which falls within Range 1, is placed on the first load cell 50a. The controller 52 then determines the distribution of the first calibration weight on each load cell and establishes a set of load weights detected on each load cell. The process 700 advances to step 708, subsequent to establishing a set of load weights for the first calibration weight, where the controller 52 repeats the placing, determining, and establishing steps (steps 702-706) for each of load cells 50. Once the first calibration weight is sequentially placed on each of the load cells 50a-50d and the corresponding set of load weights detected on each of the load cells 50a-50d are established, the controller 52 then determines a set of calibration constants $C_{R1-1}$, $C_{R1-2}$, $C_{R1-3}$, and $C_{R1-4}$ corresponding to the first calibration weight. The controller 52 saves the set of calibration constants corresponding to the first calibration weight as a set of calibration constants corresponding to Range 1 in the memory 66. The process 700 repeats previous steps 702-710 to establish a set of calibration constants that correspond to each of weight ranges and store them in the memory 66.

The process 700 then proceeds to step 602. At step 602, the controller 52 determines whether a patient weight mode is activated. If the controller 52 determines that the patient weight mode is activated, the process 600 proceeds to step 604. At step 604, the controller 52 determines an estimated patient weight using a set of calibration constants that corresponds to an initial weight range. The initial weight range may be Range 4 which corresponds to the average human weight in North America. However, it should be appreciated that the initial weight range may be manually selected by manufactures and/or caregivers.

Once the estimated patient weight is determined, the process 600 proceeds to step 606. At step 606, the controller 52 determines the weight range that corresponds to the estimated patient weight. For example, if the controller 52 determined at step 604 that the patient weight is 230 pounds, the controller 52 will determine that the 230 pounds falls within Range 5. The controller 52 then selects the corresponding set of calibration constants for Range 5 and determines the total weight using the selected set of calibration constants.

Figure 14:
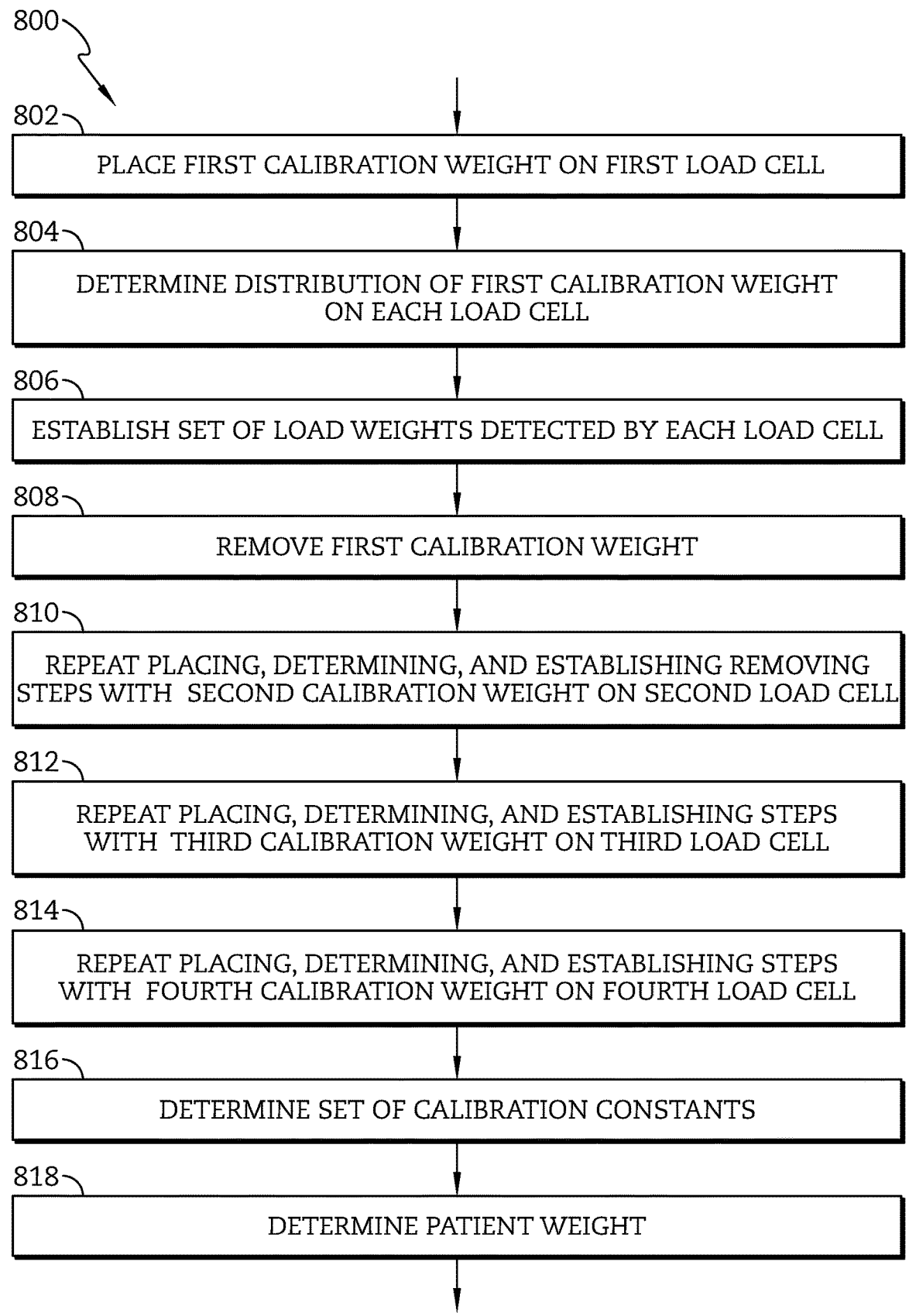
FIG. 14 is a flowchart illustrating an exemplary embodiment of a software routine for executing a patient weight mode for determining the patient weight.

In another illustrative embodiment shown in FIG. 14, the patient support apparatus 10 includes a weigh scale module 460 configured to determine the total weight of the patient. As described previously, a set of calibration constants that was determined using a single calibration weight may not be accurate for different weight ranges. To accommodate varying ranges of patient weight, the weigh scale module 460 uses at least four different calibration weights to establish sets of load weights detected by each of load cells. As shown in FIG. 14, a first calibration weight is placed on the first load cell 50a at step 802. At step 804, the controller 52 determines a distribution of the first calibration weight on each of the load cells 50a-50d and establishes a first set of load weights detected by each load cell 50. Once the first set of load weights are established for the first calibration weight, the first calibration weight is removed. Subsequent to removing the first calibration weight, a second calibration weight is placed on the second load cell 50b then the controller 52 determines a distribution of the second calibration weight on each load cell and establishes a second set of load weights detected by each load cell. Once the second set of load weights are established for the second calibration weight, the second calibration weight is removed. Placing, determining, establishing, and removing steps (steps 802-808) are repeated with a third calibration weight on the third load cell 50c and then with a fourth calibration weight on the fourth load cell 50d. For example, the first calibration weight may be 25 pounds, the second calibration weight may be 75 pounds, the third calibration weight may be 125 pounds, and the fourth calibration weight may be 175 pounds. Once the controller 52 establishes four sets of load weights that correspond to each calibration weight, the process 800 advances to step 816. At step 816, the controller 52 determines a set of calibration constants using the calibration equations (20)-(23) generated by the sets of load weights.

$$CW_1 = C_1L_1 + C_2L_2 + C_3L_3 + C_4L_4 \tag{20}$$

$$CW_2 = C_1L_1 + C_2L_2 + C_3L_3 + C_4L_4 \tag{21}$$

$$CW_3 = C_1L_1 + C_2L_2 + C_3L_3 + C_4L_4 \tag{22}$$

$$CW_4 = C_1L_1 + C_2L_2 + C_3L_3 + C_4L_4 \tag{23}$$

where $CW_1$, $CW_2$, $CW_3$, and $CW_4$ are the predefined calibration weights placed on the load cell 50a, 50b, 50c, and 50d, respectively and sequentially, each of which having a different weight, $C_1$, $C_2$, $C_3$, and $C_4$ are calibration constants for RHLC 50a, RFLC 50c, LFLC 50d, and LHLC 50b, respectively, and $L_1$, $L_2$, $L_3$, and $L_4$ are the load weights on RHLC 50a, RFLC 50c, LFLC 50d, and LHLC 50b, respectively. Accordingly, the set of calibration constants are established using a standard Gauss-Jordan or other appropriate elimination method and equations (20)-(23) are solved to obtain values for calibration constants $C_1$, $C_2$, $C_3$, and $C_4$. The resulting set of calibration constants are used to determine the total weight on the patient support surface 36.

Alternatively, in some embodiments, four different calibration weights may be loaded on each of the load cells 50a-50d at the same time. For example, a first calibration weight placed on the first load cell 50a, a second calibration weight placed on the second load cell 50a, a third calibration weight placed on the third load cell 50c, and a fourth calibration weight placed on the fourth load cell 50d. The controller 52 determines a set of load weight detected on each the load cells 50. Subsequently, the calibration weights are moved to the next load cell, such that the first calibration weight placed on the second load cell 50b, the second calibration weight placed on the third load cell 50c, the third calibration weight placed on the fourth load cell 50d, and the fourth calibration weight placed on the first load cell 50a. The controller 52 again determines a set of load weight detected on each the load cells. Subsequently, the calibration weights are moved to the next load cell, such that the first calibration weight placed on the third load cell 50c, the second calibration weight placed on the fourth load cell 50d, the third calibration weight placed on the first load cell 50a, and the fourth calibration weight placed on the second load cell 50b. The controller 52 again determines a set of load weight detected on each the load cells. Lastly, the calibration weights are moved to the next load cell 50, such that the first calibration weight placed on the fourth load cell 50d, the second calibration weight placed on the first load cell 50a, the third calibration weight placed on the second load cell 50b, and the fourth calibration weight placed on the third load cell 50c. The controller 52 again determines a set of load weight detected on each the load cells. The controller 52 determines a set of calibration constants using the calibration equations (24)-(27) generated by the sets of load weights.

$$CW_1 + CW_2 + CW_3 + CW_4 = C_1L_1 + C_2L_2 + C_3L_3 + C_4L_4 \tag{24}$$

$$CW_2 + CW_3 + CW_4 + CW_1 = C_1L_1 + C_2L_2 + C_3L_3 + C_4L_4 \tag{25}$$

$$CW_3 + CW_4 + CW_1 + CW_2 = C_1L_1 + C_2L_2 + C_3L_3 + C_4L_4 \tag{26}$$

$$CW_4 + CW_1 + CW_2 + CW_3 = C_1L_1 + C_2L_2 + C_3L_3 + C_4L_4 \tag{27}$$

where $CW_1$, $CW_2$, $CW_3$, and $CW_4$ are the different predefined calibration weights, $C_1$, $C_2$, $C_3$, and $C_4$ are calibration constants for RHLC 50a, LHLC 50b, RFLC 50c, and LFLC 50d, respectively, and $L_1$, $L_2$, $L_3$, and $L_4$ are the load weights detected on RHLC 50a, LHLC 50b, RFLC 50c, and LFLC 50d, respectively. Accordingly, the set of calibration constants are established using a standard Gauss-Jordan or other appropriate elimination method and equations (24)-(27) are solved to obtain values for calibration constants $C_1$, $C_2$, $C_3$, and $C_4$. The resulting set of calibration constants are used to determine the total weight on the patient support surface 36.

Figure 15:
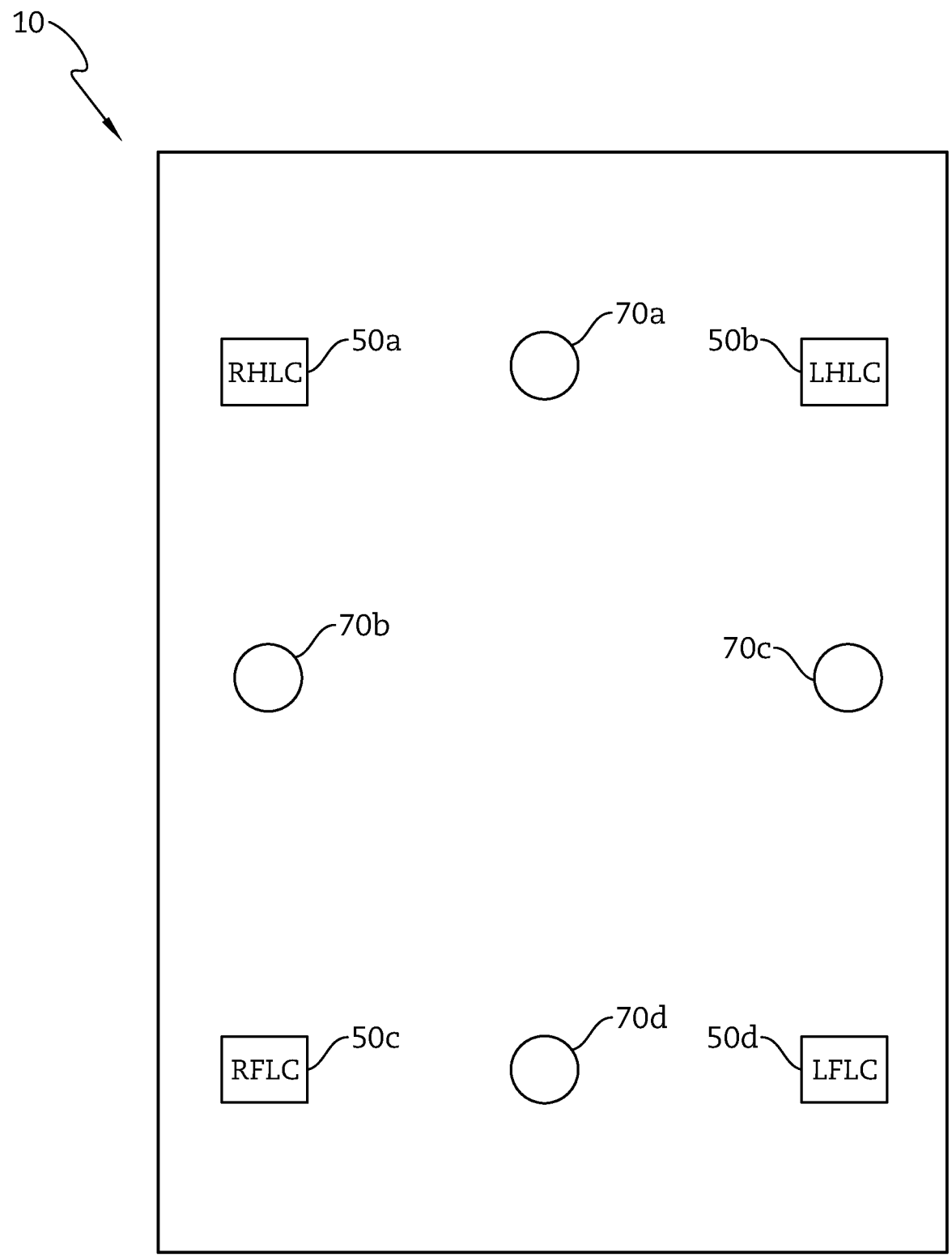
FIG. 15 is a top plan view of an embodiment of a patient support apparatus of FIG. 1 with alternative calibration positions.

As described above, the weight distribution among the load cells 50a-50d may vary depending on the position of the load exerted on the patient support surface 36. Accordingly, some embodiments may employ alternative calibration positions 70 to determine the set of calibration constants for each load cell. The alternative calibration positions 70 are predetermined and are different than the initial calibration positions 70, which correspond to the positions of the load cells 50. For example, the calibration positions may be positioned between the load cells 50. As shown in FIG. 15, a first calibration position 70a may be positioned between RHLC 50a and LHLC 50b, a second calibration position 70b may be positioned between RHLC 50a and RFLC 50c, a third calibration position 70c may be positioned between LHLC 50b and LFLC 50d, and a fourth calibration position 70d may be positioned between RFLC 50c and LFLC 50d. Accordingly, the plurality sets of load weights that correspond to each calibration position 70a-d are used to generate the calibration equations (28)-(31) set forth below.

$$CW_{70a} = C_1L_1 + C_2L_2 + C_3L_3 + C_4L_4 \tag{28}$$

$$CW_{70b} = C_1L_1 + C_2L_2 + C_3L_3 + C_4L_4 \tag{29}$$

$$CW_{70c} = C_1L_1 + C_2L_2 + C_3L_3 + C_4L_4 \tag{30}$$

$$CW_{70d} = C_1L_1 + C_2L_2 + C_3L_3 + C_4L_4 \tag{31}$$

where $CW_{70a}$, $CW_{70b}$, $CW_{70c}$, and $CW_{70d}$ are the predefined calibration weight when the predefined calibration weight is placed on the calibration position 70a, 70b, 70c, and 70d, respectively, $C_1$, $C_2$, $C_3$, and $C_4$ are calibration constants for RHLC 50a, RFLC 50c, LFLC 50d, and LHLC 50b, respectively, and $L_1$, $L_2$, $L_3$, and $L_4$ are the load weights on RHLC 50a, RFLC 50c, LFLC 50d, and LHLC 50b, respectively.

$CW_{70a}$, $CW_{70b}$, $CW_{70c}$, and $CW_{70d}$ are all equal to the predefined calibration weight. Thus, the set of calibration constants $C_1$, $C_2$, $C_3$, $C_4$ are established using a standard Gauss-Jordan or other appropriate elimination method and equations (28)-(31) are solved to obtain values for calibration constants $C_1$, $C_2$, $C_3$, and $C_4$. The set of calibration constants are used to determine the patient weight.

Figure 16:
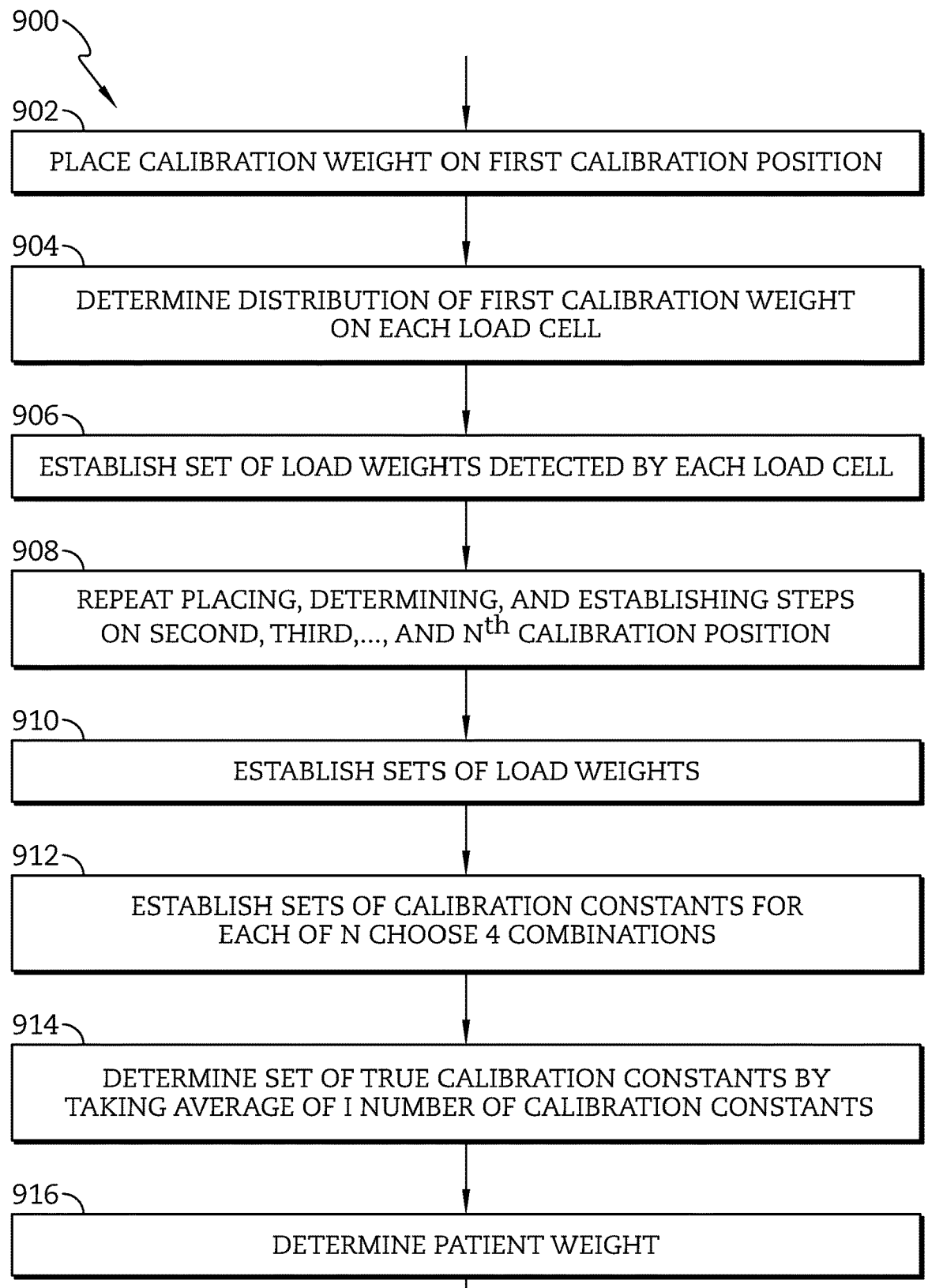
FIG. 16 is a flowchart illustrating an exemplary embodiment of a software routine for executing an n-choose-4-combination mode to determine the patient weight.

In another illustrative embodiment shown in FIGS. 16-17, the patient support apparatus 10 includes a weigh scale module 560 configured to determine the weight of the patient. In this embodiment, instead of having a fixed number of predefined calibration positions, there are n number of calibration positions 70 on the patient support surface 36. Each calibration position 70 is distinct from all other calibration position 70 and it may not be predetermined. Accordingly, a predetermined calibration weight is placed on a first calibration position 70a and a distribution of the predefined calibration weight corresponds to the first calibration position 70a on each load cell 50a-50d is determined, as shown in FIG. 16, steps 902-604. Subsequently, the set of load weights detected by each load cell is established at step 906. The predetermined calibration weight is then placed on a second calibration position 70b and the distribution of the predefined calibration weight corresponds to the second calibration position 70b is determined. The placing, determining, and establishing steps are repeated for each of the calibration position 70a-n until the distribution of the predefined calibration weight corresponds to a $n^{th}$ calibration position 70n is determined.

$$CP_1 = C_1L_1 + C_2L_2 + C_3L_3 + C_4L_4 \quad (32)$$

$$CP_2 = C_1L_1 + C_2L_2 + C_3L_3 + C_4L_4 \quad (33)$$

$$CP_3 = C_1L_1 + C_2L_2 + C_3L_3 + C_4L_4 \quad (34)$$

$$CP_n = C_1L_1 + C_2L_2 + C_3L_3 + C_4L_4 \quad (35)$$

where $CP_1$, $CP_2$, $CP_3$, ..., and $CP_n$ are the predefined calibration weight when the predefined calibration weight is placed on the calibration positions 70a, 70b, 70c, ..., 70n, respectively; $C_1$, $C_2$, $C_3$, and $C_4$ are calibration constants for RHLC 50a, LHLC 50b, RFLC 50c, and LFLC 50d, respectively; and $L_1$, $L_2$, $L_3$, and $L_4$ are the load weights on for RHLC 50a, LHLC 50b, RFLC 50c, and LFLC 50d, respectively. $CP_1$, $CP_2$, $CP_3$, ..., and $CP_n$ are all equal to the predefined calibration weight.

Since there are four calibration constants, each of which corresponds to each load cell, with n number of calibration positions, there are n choose 4 combinations (i) available for determining a set of calibration constants. Once i combinations are established, there are i number of the calibration constants for each load cell. "True" calibration constants $C_1$, $C_2$, $C_3$, $C_4$ is determined by taking the average calibration constants for each load cell as shown in equations (36)-(39).

$$C_1 = \frac{C_{1-1} + C_{1-2} + C_{1-3} + \ldots + C_{1-i}}{i} \quad (36)$$

$$C_2 = \frac{C_{2-1} + C_{2-2} + C_{2-3} + \ldots + C_{2-i}}{i} \quad (37)$$

$$C_3 = \frac{C_{3-1} + C_{3-2} + C_{3-3} + \ldots + C_{3-i}}{i} \quad (38)$$

$$C_4 = \frac{C_{4-1} + C_{4-2} + C_{4-3} + \ldots + C_{4-i}}{i} \quad (39)$$

where $i = \binom{n}{4}, n \geq 5$.

For example, if there are 5 calibration positions (n=5), the distribution of predefined each calibration position.

$$CP_1 = C_1L_1 + C_2L_2 + C_3L_3 + C_4L_4 \quad (40)$$

$$CP_2 = C_1L_1 + C_2L_2 + C_3L_3 + C_4L_4 \quad (41)$$

$$CP_3 = C_1L_1 + C_2L_2 + C_3L_3 + C_4L_4 \quad (42)$$

$$CP_4 = C_1L_1 + C_2L_2 + C_3L_3 + C_4L_4 \quad (43)$$

$$CP_5 = C_1L_1 + C_2L_2 + C_3L_3 + C_4L_4 \quad (44)$$

where $CP_1$, $CP_2$, $CP_3$, $CP_4$, and $CP_5$ are the predefined calibration weight when the predefined calibration weight is placed on one of the five calibration positions; $C_1$, $C_2$, $C_3$, and $C_4$ are calibration constants for RHLC 50a, LHLC 50b, RFLC 50c, and LFLC 50d, respectively; and $L_1$, $L_2$, $L_3$, and $L_4$ are the load weights on for RHLC 50a, LHLC 50b, RFLC 50c, and LFLC 50d, respectively. $CP_1$, $CP_2$, $CP_3$, $CP_4$, and $CP_5$ are all equal to the predefined calibration weight.

Because 5 choose 4 is 5, five different combinations, i=5, of $CP_1$, $CP_2$, $CP_3$, $CP_4$, and $CP_5$ to determine a set of calibration constants $C_1$, $C_2$, $C_3$, $C_4$: ($CP_1$, $CP_2$, $CP_3$, $CP_4$), ($CP_1$, $CP_2$, $CP_3$, $CP_5$), ($CP_1$, $CP_2$, $CP_4$, $CP_5$), ($CP_1$, $CP_3$, $CP_4$, $CP_5$), and ($CP_2$, $CP_3$, $CP_4$, $CP_5$). For each of these combinations, a set calibration constants $C_1$, $C_2$, $C_3$, $C_4$ is established using a standard Gauss-Jordan or other appropriate elimination method and corresponding equations (40)-(44) are solved to obtain values for calibration constants $C_1$, $C_2$, $C_3$, and $C_4$. Because there are five possible combinations, five sets of calibration constants are established: ($C_{1-1}$, $C_{2-1}$, $C_{3-1}$, $C_{4-1}$), ($C_{1-2}$, $C_{2-2}$, $C_{3-2}$, $C_{4-2}$), ($C_{1-3}$, $C_{2-3}$, $C_{3-3}$, $C_{4-3}$), ($C_{1-4}$, $C_{2-4}$, $C_{3-4}$, $C_{4-4}$), and ($C_{1-5}$, $C_{2-5}$, $C_{3-5}$, $C_{4-5}$). At step 914, the controller 52 calculates the average calibration constant for each load cell to determine the "true" calibration constant for that load cell.

$$C_{T1} = \frac{C_{1-1} + C_{1-2} + C_{1-3} + C_{1-4} + C_{1-5}}{5} \quad (45)$$

$$C_{T2} = \frac{C_{2-1} + C_{2-2} + C_{2-3} + C_{2-4} + C_{2-5}}{5} \quad (46)$$

$$C_{T3} = \frac{C_{3-1} + C_{3-2} + C_{3-3} + C_{3-4} + C_{3-5}}{5} \quad (47)$$

$$C_{T4} = \frac{C_{4-1} + C_{4-2} + C_{4-3} + C_{4-4} + C_{4-5}}{5} \quad (48)$$

where $C_{T1}$, $C_{T2}$, $C_{T3}$, and $C_{T4}$ are the "true" calibration constant for RHLC 50a, LHLC 50b, RFLC 50c, and LFLC 50d, respectively. Lastly, the process 900 proceeds to step 916 to determine the total weight using the set of true calibration constants.

Although certain illustrative embodiments and graphical illustrations have been described in detail above, variations and modifications exist within the scope and spirit of this disclosure as described and as defined in the following claims.

The invention claimed is:

1. A patient support apparatus, comprising
a weigh frame,
a base support frame, a plurality of load cells supporting the weigh frame on the base support frame such that a load supported by the weigh frame is supported by the load cells, each load cell configured to produce a signal indicative of a load weight bearing upon that load cell, and a controller coupled to the load cells to determine a total weight supported by the load cells, wherein a calibration constant for each respective load cell is determined dynamically by varying the magnitude of at least one calibration weight positioned on the weigh frame during a calibration process, wherein the controller comprises a processor and a memory device coupled to the processor, the memory device including instructions that, when processed by the processor, cause the processor to consider the signal from each load cell and dynamically determines the calibration constants for the respective load cells by (i) detecting a predefined calibration weight on a patient support surface at one of "n" calibration positions, wherein n is a numerical number greater than four, (ii) measuring a current weight distribution of the predefined calibration weight on each of the load cells, (iii) storing a set of load weights for respective load cells that corresponds to the current distribution of the predefined calibration weight for each of the load cells, (iv) detecting the predefined calibration weight has been placed at a subsequent predetermined calibration positions and executing (ii) and (iii) steps at each subsequent calibration position, (v) selecting, subsequent to establishing "n" sets of calibration constants for each of the load cells, four sets of calibration constants randomly from the "n" sets of calibration constants, and (vi) determining a set of calibration constants for respective load cells by averaging the selected calibration constants.

2. The patient support apparatus of claim 1, wherein the controller is configured to determine an actual weight of the patient supported on the patient support apparatus by using the determined set of calibration constants for respective load cells.

3. The patient support apparatus of claim 1, wherein the controller is configured to trigger an alarm when a rate of change in patient position exceeds an alarm threshold.

4. The patient support apparatus of claim 3, wherein the alarm threshold depends on a patient activity level.

5. The patient support apparatus of claim 4, wherein the controller further comprises a memory configured to store a plurality of alarm thresholds that corresponds to each patient activity level.

6. The patient support apparatus of claim 4, wherein the patient activity level is predefined by a user.

7. The patient support apparatus of claim 4, wherein the controller is configured to determine the patient activity level by determining a rate of change in the weight distribution on each of the plurality of load cells for a predetermined time period.

8. A patient support apparatus, comprising
a weigh frame, a plurality of load cells supporting the weigh frame such that a load supported by the weigh frame is supported by the load cells, each load cell configured to produce a signal indicative of a load weight bearing upon that load cell, and a controller coupled to the load cells to determine a total weight supported by the load cells, wherein a calibration constant for each respective load cell is determined dynamically by varying the magnitude of at least one calibration weight positioned on the weigh frame during a calibration process, wherein the controller comprises a processor and a memory device coupled to the processor, the memory device including instructions that, when processed by the processor, cause the processor to consider the signal from each load cell and dynamically determines the calibration constants for the respective load cells by (i) detecting a predefined calibration weight on a patient support surface at one of "n" calibration positions, wherein n is a numerical number greater than four, (ii) measuring a current weight distribution of the predefined calibration weight on each of the load cells, (iii) storing a set of load weights for respective load cells that corresponds to the current distribution of the predefined calibration weight for each of the load cells, (iv) detecting the predefined calibration weight has been placed at a subsequent predetermined calibration positions and executing (ii) and (iii) steps at each subsequent calibration position, (v) selecting, subsequent to establishing "n" sets of calibration constants for each of the load cells, four sets of calibration constants randomly from the "n" sets of calibration constants, and (vi) determining a set of calibration constants for respective load cells by averaging the selected calibration constants.

9. The patient support apparatus of claim 8, wherein the controller is configured to determine an actual weight of the patient supported on the patient support apparatus by using the determined set of calibration constants for respective load cells.

10. The patient support apparatus of claim 8, wherein the controller is configured to trigger an alarm when a rate of change in patient position exceeds an alarm threshold.

11. The patient support apparatus of claim 10, wherein the alarm threshold depends on a patient activity level.

12. The patient support apparatus of claim 11, wherein the controller further comprises a memory configured to store a plurality of alarm thresholds that corresponds to each patient activity level.

13. The patient support apparatus of claim 11, wherein the patient activity level is predefined by a user.

14. The patient support apparatus of claim 11, wherein the controller is configured to determine the patient activity level by determining a rate of change in the weight distribution on each of the plurality of load cells for a predetermined time period.

* * * * *